United States Patent
Segal et al.

(10) Patent No.: US 10,361,003 B2
(45) Date of Patent: Jul. 23, 2019

(54) METHOD AND APPARATUS FOR PREDICTING RESPONSE TO FOOD

(71) Applicant: Yeda Research and Development Co. Ltd., Rehovot (IL)

(72) Inventors: Eran Segal, Ramat-HaSharon (IL); Eran Elinav, Mazkeret Batia (IL)

(73) Assignee: Yeda Research and Development Co. Ltd., Rehovot (IL)

( * ) Notice: Subject to any disclaimer, the term of this patent is extended or adjusted under 35 U.S.C. 154(b) by 449 days.

(21) Appl. No.: 15/022,643

(22) PCT Filed: Apr. 28, 2015

(86) PCT No.: PCT/IL2015/050439
§ 371 (c)(1),
(2) Date: Mar. 17, 2016

(87) PCT Pub. No.: WO2015/166489
PCT Pub. Date: Nov. 5, 2015

(65) Prior Publication Data
US 2016/0232311 A1    Aug. 11, 2016

Related U.S. Application Data

(60) Provisional application No. 61/984,944, filed on Apr. 28, 2014.

(51) Int. Cl.
*G16H 50/20*    (2018.01)
*G16H 50/70*    (2018.01)
(Continued)

(52) U.S. Cl.
CPC ......... *G16H 50/20* (2018.01); *G06F 19/3475* (2013.01); *G06N 20/00* (2019.01); *G16H 50/70* (2018.01); *Y02A 90/26* (2018.01)

(58) Field of Classification Search
CPC ........ G16H 50/20; G16H 50/70; G01F 19/00; G06F 19/3475; G06N 99/005; Y02A 90/26
See application file for complete search history.

(56) References Cited

U.S. PATENT DOCUMENTS 6,063,820 A    5/2000   Cavazza
8,762,167 B2   6/2014   Blander et al.
(Continued)

FOREIGN PATENT DOCUMENTS

CN    104415061    3/2015
EP     2006786    12/2008
(Continued)

OTHER PUBLICATIONS

Communication Relating to the Results of the Partial International Search dated Aug. 14, 2015 From the International Searching Authority Re. Application No. PCT/IL2015/050442.
(Continued)

*Primary Examiner* — Phuc T Dang

(57) ABSTRACT

Method of predicting a response of a subject to food is disclosed. The method comprises: selecting a food to which a response of the subject is unknown; accessing a first database having data describing the subject but not a response of the subject to the selected food; accessing a second database having data pertaining to responses of other subjects to foods, the responses of the other subjects including responses of at least one other subject to the selected food or a food similar to said selected food; and analyzing the databases based on the selected food to estimate the response of the subject to the selected food.

46 Claims, 22 Drawing Sheets
(19 of 22 Drawing Sheet(s) Filed in Color)

(51) Int. Cl.
G06N 20/00 (2019.01)
G06F 19/00 (2018.01)

(56) References Cited

U.S. PATENT DOCUMENTS

| | | | |
|---|---|---|---|
| 9,301,983 | B2 | 4/2016 | Huang et al. |
| 2003/0208113 | A1 | 11/2003 | Mault et al. |
| 2004/0221855 | A1 | 11/2004 | Ashton |
| 2008/0082584 | A1 | 4/2008 | Jung et al. |
| 2009/0136454 | A1 | 5/2009 | Versalovic et al. |
| 2010/0172874 | A1 | 7/2010 | Turnbaugh et al. |
| 2012/0264637 | A1 | 10/2012 | Wiener-Kronish et al. |
| 2013/0224155 | A1 | 8/2013 | Kaplan et al. |
| 2013/0337086 | A1 | 12/2013 | Goolsbee et al. |
| 2014/0024132 | A1 | 1/2014 | Jia et al. |
| 2014/0073610 | A1 | 3/2014 | Ekwuribe |
| 2014/0179726 | A1 | 6/2014 | Bajaj et al. |
| 2014/0212492 | A1 | 7/2014 | Mateescu et al. |
| 2015/0213193 | A1 | 7/2015 | Apte et al. |
| 2015/0216913 | A1 | 8/2015 | Herranz et al. |
| 2015/0259728 | A1 | 9/2015 | Cutliffe et al. |
| 2016/0263166 | A1 | 9/2016 | Elinav et al. |
| 2018/0140648 | A1 | 5/2018 | Segal et al. |
| 2018/0148770 | A1 | 5/2018 | Elinav et al. |
| 2019/0022152 | A1 | 1/2019 | Elinav et al. |

FOREIGN PATENT DOCUMENTS

| | | |
|---|---|---|
| WO | WO 02/05702 | 1/2002 |
| WO | WO 02/07741 | 1/2002 |
| WO | WO 02/100266 | 12/2002 |
| WO | WO 2006/079124 | 7/2006 |
| WO | WO 2011/041892 | 4/2011 |
| WO | WO 2013/175038 | 12/2013 |
| WO | WO 2014/196913 | 12/2014 |
| WO | WO 2015/166489 | 11/2015 |
| WO | WO 2015/166492 | 11/2015 |
| WO | WO 2016/174677 | 11/2016 |
| WO | WO 2016/185469 | 11/2016 |

OTHER PUBLICATIONS

Communication Relating to the Results of the Partial International Search dated Jul. 28, 2015 From the International Searching Authority Re. Application No. PCT/IL2015/050439.
Communication Relating to the Results of the Partial International Search dated Aug. 8, 2016 From the International Searching Authority Re. Application No. PCT/IL2016/050520.
International Search Report and the Written Opinion dated Oct. 19, 2015 From the International Searching Authority Re. Application No. PCT/IL2015/050349.
International Search Report and the Written Opinion dated Oct. 20, 2015 From the International Searching Authority Re. Application No. PCT/IL2015/050442.
Invitation to Pay Additional Fees dated Jul. 22, 2016 From the International Searching Authority Re. Application No. PCT/IL2016/050442.
Barret et al. "Probiotics: A Potential Role in the Prevention of Gestational Diabetes?", Acta Diabctoogica, XP035153202, 49(1): 1-13, Nov. 21, 2012. p. 3.
Calcinaro et al. "Oral Probiotic Administration Induces Interleukin-10 Production and Prevents Spontaneous Autoimmune Diabetes in the Non-Obese Diabetic Mouse", Diabetologia; XP19322640, 48(8): 1565-1575, Aug. 1, 2005. p. 1566.
Cao et al. "The Role of Commensal Bacteria in the Regulation of Sensitization to Food Allergens", FEBS Letters, XP029083055, 588(22): 4258-4266, Available Online May 1, 2014.
Colitis IQ "Treatment for Colitis With Antihistamines", Colitis IQ, 2 P., Apr. 21, 2010.
Cowan et al. "Artificial Sweetener Consumption Differentially Affects the Gut Microbiota-Host Metabolic Interactions", The FASEB Journal, XP055205066, 27: # 224.7, Apr. 2013.

Ding et al. "Edible Composition Used as Medicine and Food for e.g. Regulating Animal Intestinal Channel Comprises Inulin and Clostridium Butyricum", Database WPI [Online], XP002760121, AN 2015-281247, Mar. 18, 2015.
Hajela et al. "Probiotic Foods: Can their Increasing Use In India Ameliorate the Burden of Chronic Lifestyle Disorders?", Indian Journal of Medical Research, XP009191 061,139(1): 19-26, Jan. 1, 2014. p. 20.
Ivey et al. "The Effects of Probiotic Bacteria on Glycaemic Control in Overweight Men and Women: A Ranodmized Controlled Trial", European Journal of Clinical Nutrition, 68: 447-452, Published Online Feb. 26, 2014.
Mayo Foundation "Microbiome Program", Mayo Clinic Center for Individualized Medicine, Mayo Foundation fro Medical Education and Research, 6 P., 1998-2014.
Morris et al. "Identification of Differential Responses to an Oral Glucose Tolerance Test in Healthy Adults", PLoS ONE, 8(8): e72890-1-e72890-9, Aug. 22, 2013.
Palmnaes et al. "Low-Dose Aspartame Consumption Differentially Affects Gut Microbiota-Host Metabolic Interactions in the Diet-Induced Obese Rat", PLOS ONE, XP055205532, 9(10): e109841-1-e109841-10, Oct. 14, 2014.
Payne et al. "Gut Microbial Adaption to Dietary Consumption of Fructose, Artificial Sweeteners and Sugar Alcohols: Implications for Host-Microbe Interactions Contributing to Obesity", Obesity Reviews, XP055205060, 13(9): 799-809, Jun. 11, 2012. Abstract, p. 803, Table 3, Left col., Last Para-Right col., Last Para, p. 807, Left Col.
Segal et al. "Glucose and Health", Medtronics Diabetes UK, 7 P., Sep. 8, 2013.
Shimizu et al. "Dietary Taurine Attenuates Dextran Sulfate Sodium (DSS)-Induced Experimental Colitis in Mice", Taurine 7, Advances in Experimental Medicine and Biology, 643(Chap.27): 265-271, 2009.
Suez et al. "Artificial Sweeteners Induce Glucose Intolerance by Altering the Gut Microbiota", Nature, XP055205484, 514: 181-188 & 10 P. Article Research, Published Online Sep. 17, 2014.
Suez et al. "Non-Caloric Artificial Sweeteners and the Microbiome: Findings and Challenges", Gut Microbes, XP008177160, 6(2): 149-155, Published Online Apr. 1, 2015.
Thaiss et al. "A Day in the Life of the Meta-Organism: Diurnal Rhythms of the Intestinal Microbiome and Its Host", Gut Microbes, XP008177161, 6(2): 137-142, Published Online Apr. 22, 2015.
Thaiss et al. "Transkingdom Control of Microbiota Diurnal Oscillations Promotes Metabolic Homeostasis", Cell, XP029084863, 159(3): 514-529, Oct. 23, 2014.
Thompson-Chagoyan et al. "Faecal Microbiota and Short-Chain Fatty Acid Leves in Faeces From Infants With Cow's Milk Protein Allergy", International Archives of Allergy and Immunology, XP009166971, 156(3): 325-332, Published Online Jun. 29, 2011. Abstract, Sentence Bridging p. 325-326, p. 327, Left col., Last Para Right col., 3rd Para: 'Fish of Bacterial Cells', Right col., Last Para: 'Determination of Faecal SCFA', p. 328, Right col., Para 2: 'Bacterial Counts (FISH-FC)' and Table 3, p. 328, Right col., Last Para-p. 329, right col., Last Para, p. 330, Table 4.
International Search Report and the Written Opinion dated Oct. 4, 2016 From the International Searching Authority Re. Application No. PCT/IL2016/050520.
International Search Report and the Written Opinion dated Sep. 30, 2016 From the International Searching Authority Re. Application No. PCT/IL2016/050442.
Field et al. "Measurement of Fecal Corticosterone Metabolites as a Predictor of the Habituation of Rhesus Macaques (Macaca Mulatta) to Jacketing", Journal of the American Association for Laboratory Animal Science, 54(1): 59-65, Jan. 2015. Abstract, p. 61, col. 1, Para 6.
Kim et al. "Implication of Intestinal VDR Deficiency in Inflammatory Bowel Disease", Biochimica et Biophysica Acta, 1830(1):2118-2128, Published Online Oct. 2, 2012. Abstract, p. 2, Para 4, p. 5, Para 4, p. 6, Paras 2-3, p. 8, Paras 2, 4, Figs.5A-5C.
International Preliminary Report on Patentability dated Nov. 10, 2016 From the International Bureau of WIPO Re. Application No. PCT/IL2015/050349. (12 Pages).

(56) References Cited

OTHER PUBLICATIONS

International Preliminary Report on Patentability dated Nov. 10, 2016 From the International Bureau of WIPO Re. Application No. PCT/IL2015/050442. (13 Pages).
Restriction Official Action dated Oct. 4, 2017 From the US Patent and Trademark Office Re. U.S. Appl. No. 15/030,650. (12 Pages).
International Preliminary Report on Patentability dated Nov. 9, 2017 From the International Bureau of WIPO Re. Application No. PCT/IL2016/050442. (12 Pages).
Communication Under Rule 164(2)(a) EPC dated Nov. 30, 2017 From the European Patent Office Re. Application No. 15727472.1. (4 Pages)
International Preliminary Report on Patentability dated Nov. 30, 2017 From the International Bureau of WIPO Re. Application No. PCT/IL2016/050520. (19 Pages).
Official Action dated Apr. 4, 2018 From the US Patent and Trademark Office Re. U.S. Appl. No. 15/030,650. (52 pages).
Koletzko et al. "Global Standard for the Composition of Infant Formula: Recommendations of an ESPGHAN Coordinated International Expert Group", Journal of Pediatric Gastroenterology and Nutrition, 41:584-599, Nov. 2005.
Communication Pursuant to Article 94(3) EPC dated Apr. 13, 2018 From the European Patent Office Re. Application No. 15727472.1. (10 Pages).
Restriction Official Action dated May 17, 2018 From the US Patent and Trademark Office Re. U.S. Appl. No. 15/568,818. (11 pages).
Fray et al. "A Combination of Aloe Vera, Curcumin, Vitamin C, and Taurine Increases Canine Fibroblast Migration and Decreases Tritiated Water Diffusion across Canine Keratinocytes In Vitro", The Journal of Nutrition, 134(8): 2117S-2119S, Aug. 2004.
Invitation to Respond to Written Opinion dated Jul. 3, 2018 from the Intellectual Property Office of Singapore Re. Application No. 11201709456R. (13 pages).
Official Action dated Aug. 8, 2018 From the US Patent and Trademark Office Re. U.S. Appl. No. 15/568,818. (23 pages).
Bjerrum et al. "Metabonomics of Human Fecal Extracts Characterize Ulcerative Colitis, Crohn's Disease and Healthy Individuals", Metabolomics, 11:122-133, 2015.
Giris et al. Effect of Taurine on Oxidative Stress and Apoptosis-Related Protein Expression in Trinitrobenzene Sulphonic Add-Induced Colitis, Clinical and Experimental Immunology,15:102-110, 2008.
Kolho et al. "Faecal and Serum Metabolomics in Paediatric Inflammatory Bowel Disease", Journal of Crohn 'sand Colitis, 11(3): 321-334, Mar. 1, 2017.
Le Gall et al. "Metabolomics of Fecal Extracts Detects Altered Metabolic Activity of Gut Microbiota in Ulcerative Colitis and Irritable Bowel Syndrome", Journal of Proteome, 10(9): 4208-4218, Published Jul. 18, 2011.
Zhao et al. "Attenuation by Dietary Taurine of Dextran Sulfate Sodium-Induced Colitis in Mice and of THP1 Induced Damage to Intestinal Caco-2 Ceil Monolayers", Amino Acids 35: 217-224, 2007.
Notification of Office Action and Search Report dated Aug. 28, 2018 From the State Intellectual Property Office of the People's Republic of China Re. Application No. 201580022088.X. (11 Pages).
Office Action dated Oct. 3, 2018 From the Israel Patent Office Re. Application No. 247794 and Its Translation Into English. (6 Pages).
Translation dated Sep. 17, 2018 of Notification of Office Action and Search Report dated Aug. 28, 2018 From the State Intellectual Property Office of the People's Republic of China Re. Application No. 201580022088.X. (21 Pages).
Restriction Official Action dated Jan. 10, 2019 From the US Patent and Trademark Office Re. U.S. Appl. No. 15/575,827. (9 pages).
Official Action dated Jan. 31, 2019 From the US Patent and Trademark Office Re. U.S. Appl. No. 15/568,818. (22 Pages).
Communication Pursuant to Rule 164(1) EPC [Supplementary Partial European Search Report and the Provisional Opinion] dated Dec. 12, 2018 From the European Patent Office Re. Application No. 16786074.1. (12 Pages).
Mayeur et al. "Faecal D/L Lactate Ration Is A Metabolic Signature of Microbiota Imbalance in Patients With Short Bowel Syndrome", PLOS ONE, XP055524126, 8(1): e54335-1-e54335-12, Published Online Jan. 23, 2013. Title, Abstract, Fig.2, p. 9, Last Para, Conclusion.
Communication Pursuant to Rule 164(2)(b) and Article 94(3) EPC dated Jul. 25, 2018 From the European Patent Office Re. Application No. 15725898.9. (12 Pages).
Supplementary European Search Report and the European Search Opinion dated Mar. 15, 2019 From the European Patent Office Re. Application No. 16786074.1. (11 Pages).

FIG. 2A

| Food 1 | Response to food 1 |
| Food 2 | Response to food 2 |
| ⋮ | ⋮ |
| Food N | Response to food N |

FIG. 2B

| | Food 1 | Response to food 1 |
| Subject 1 | ⋮ | ⋮ |
| | Food $N_1$ | Response to food $N_1$ |
| ⋮ | ⋮ | ⋮ |
| | Food 1 | Response to food 1 |
| Subject M | ⋮ | ⋮ |
| | Food $N_M$ | Response to food $N_M$ |

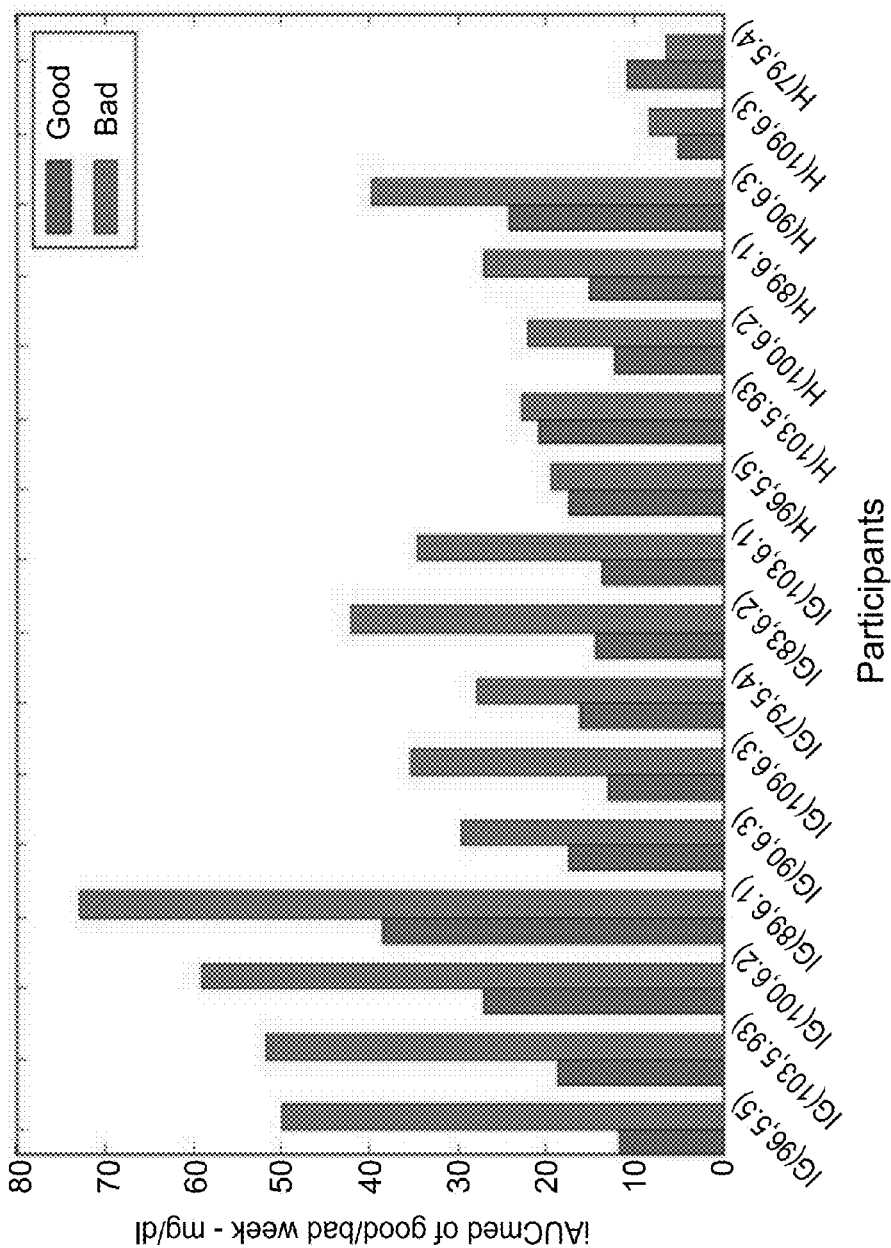

METHOD AND APPARATUS FOR PREDICTING RESPONSE TO FOOD

RELATED APPLICATIONS

This application is a National Phase of PCT Patent Application No. PCT/IL2015/050439 having International filing date of Apr. 28, 2015, which claims the benefit of priority under 35 USC § 119(e) of U.S. Provisional Patent Application No. 61/984,944 filed on Apr. 28, 2014. The contents of the above applications are all incorporated by reference as if fully set forth herein in their entirety.

FIELD AND BACKGROUND OF THE INVENTION

The present invention, in some embodiments thereof, relates to nutrition and, more particularly, but not exclusively, to a method and apparatus for predicting a response of a subject to one or more foods.

The prevalence of obesity in adults, children and adolescents has increased rapidly over the past 30 years and continues to rise. Obesity is classically defined based on the percentage of body fat or, more recently, the body mass index (BMI), defined as the ratio of weight (Kg) divided by height (in meters) squared.

Overweight and obesity are associated with increasing the risk of developing many chronic diseases of aging. Such co-morbidities include type 2 diabetes mellitus, hypertension, coronary heart diseases and dyslipidemia, gallstones and cholecystectomy, osteoarthritis, cancer (of the breast, colon, endometrial, prostate, and gallbladder), and sleep apnea. It is recognized that the key to reducing the severity of the diseases is to lose weight effectively. Although about 30 to 40% claim to be trying to lose weight or maintain lost weight, current therapies appear not to be working. Besides dietary manipulation, pharmacological management and in extreme cases, surgery, are sanctioned adjunctive therapies to treat overweight and obese patients. Drugs have side effects, and surgery, although effective, is a drastic measure and reserved for morbidly obese.

Morris et al. ["Identification of Differential Responses to an Oral Glucose Tolerance Test in Healthy Adults," 2013, PLoS ONE 8(8): e72890] identified differential responders to an oral glucose tolerance test (OGTT). Four distinct metabolic responses to the OGTT were found and were characterized by different levels of BMI, body fat and maximal oxygen consumption.

International Publication No. WO2002100266 discloses a dietary technique which employs a database of reference human factors. A computer receives user data on the human factors and predicts a selected characteristic of blood of the user dependent upon user data and measured blood characteristics, to generate a prediction model. The prediction model is then interrogated to generate and display a predicted blood characteristic dependent upon input human factor data. Also disclosed is the use of a database which includes a prediction model on a selected blood characteristic as a function of a human factor.

International Publication No. WO2006079124 discloses characterization of foodstuffs and/or exercise in terms of units of energy, in which the quantity of energy in linear units that is associated with an ingested foodstuff is directly proportional to the resultant blood sugar absorbed into the blood of a Type 1 diabetic. Also disclosed is characterization of exercise in terms of linear units, such that the quantity of energy in linear units that is expended by a person during exercise, is directly proportional to the resultant decrease in their blood sugar level.

SUMMARY OF THE INVENTION

According to an aspect of some embodiments of the present invention there is a method of predicting a response of a subject to food. The method comprises: selecting a food to which a response of the subject is unknown; accessing a first database having data describing the subject but not a response of the subject to the selected food; accessing a second database having data pertaining to responses of other subjects to foods; and analyzing the databases based on the selected food to estimate the response of the subject to the selected food.

According to some embodiments of the invention the first database comprises data pertaining to responses of the subject to foods, each food being other than the selected food.

According to an aspect of some embodiments of the present invention there is provided a method of predicting a response of a subject to food. The method comprises: selecting a food and a context of food intake for which a response of the subject is unknown; accessing a first database having data having data describing the subject but not a response of the subject to the selected food within the selected context of food intake; accessing a second database having data pertaining to responses of other subjects to foods, the responses of the other subjects including responses of at least one other subject to the selected food; and analyzing the databases based on the selected food to estimate the response of the subject to the selected food within the selected context of food intake.

According to some embodiments of the invention the first database comprises data pertaining to responses of the subject to foods within respective contexts of food intake, each food being other than the selected food within the selected context of food intake.

According to some embodiments of the invention the context of food intake is selected from the group consisting of an amount of the food, a time of day, a time before or after sleep, a time before or after exercise, a mental or physiological condition, and an environmental condition.

According to some embodiments of the invention the responses of the other subjects including responses of at least one other subject to the selected food.

According to some embodiments of the invention the second database is devoid of any response of any other subject to the selected food.

According to some embodiments of the invention the analysis comprises executing a machine learning procedure.

According to some embodiments of the invention the second database comprises data classified according to a predetermined set of classification groups, wherein the analysis comprises classifying the subject according to the set of classification groups, to provide a classification group being specific to the subject, and wherein the response of the subject to the selected food is estimated based on responses in the second database that correspond to the classification group.

According to some embodiments of the invention at least one of the first and the second databases comprises one or more multidimensional entries, each entry having at least three dimensions. According to some embodiments of the invention at least one of the first and the second databases comprises one or more multidimensional entries, each entry having at least four dimensions. According to some embodiments of the invention at least one of the first and the second databases comprises one or more multidimensional entries, each entry having at least five dimensions.

According to some embodiments of the invention at least one of the first and the second databases comprises one or more multidimensional entries, each entry corresponding to an individual and comprises a food consumed by the individual and at least a glycemic response of the individual to the food.

According to some embodiments of the invention at least one of the first and the second databases comprises one or more multidimensional entries, each entry corresponding to an individual being characterized in the respective database by at least a partial microbiome profile of the individual.

According to some embodiments of the invention at least one of the first and the second databases comprises one or more multidimensional entries, each entry corresponding to an individual and comprises a food consumed by the individual and at least a characteristic intake frequency associated with the food.

According to some embodiments of the invention at least one of the first and the second databases comprises one or more multidimensional entries, each entry corresponding to an individual and comprises a food consumed by the individual and at least a partial chemical composition of the food.

According to some embodiments of the invention at least one of the first and the second databases comprises one or more multidimensional entries, each entry corresponding to an individual being characterized in the respective database by at least a partial blood chemistry of the individual.

According to some embodiments of the invention at least one of the first and the second databases comprises one or more multidimensional entries, each entry corresponding to an individual being characterized in the respective database by at least a genetic profile of the individual.

According to some embodiments of the invention at least one of the first and the second databases comprises one or more multidimensional entries, each entry corresponding to an individual being characterized in the respective database by at least metabolomic data associated with the individual.

According to some embodiments of the invention at least one of the first and the second databases comprises one or more multidimensional entries, each entry corresponding to an individual being characterized in the respective database by at least a medical condition of the individual.

According to some embodiments of the invention at least one of the first and the second databases comprises one or more multidimensional entries, each entry corresponding to an individual being characterized in the respective database by at least food intake habits of the individual.

According to some embodiments of the invention at least one of the first and the second databases comprises one or more multidimensional entries, each entry corresponding to an individual, and comprises a listing of activities performed by the individual over a time period.

According to an aspect of some embodiments of the present invention there is provided a computer software product, comprising a computer-readable medium in which program instructions are stored, which instructions, when read by a data processor, cause the data processor to receive a food to which a response of a subject is unknown, and to execute the method as delineated above and optionally as detailed below.

According to an aspect of some embodiments of the present invention there is provided apparatus for predicting a response of a subject to food. The apparatus comprising: a user interface configured to receive a food to which a response of the subject is unknown, and a data processor having a computer-readable medium storing the computer software product.

According to an aspect of some embodiments of the present invention there is provided a method of constructing a database. The method comprises, for each subject of a group of subjects: monitoring glucose levels of the subject over a time period of at least a few days; monitoring foods consumed by the subject over the time period; analyzing the monitored glucose levels and the monitored foods to associate a glycemic response to each food of at least a portion of the consumed foods; and making a database record pertaining to the association in at least one database.

According to some embodiments of the invention the method wherein the at least one database comprises a group database corresponding to all subjects in the group of subject.

According to some embodiments of the invention for at least one subject, the at least one database also comprises a subject-specific database corresponding to the subject.

According to some embodiments of the invention the method comprises obtaining additional data pertaining to the subject and/or the food and making a record of the additional data in the at least one database.

According to some embodiments of the invention the method comprises processing the at least one database using a multidimensional analysis procedure, and updating the at least one database responsively to the analysis.

According to some embodiments of the invention the multidimensional analysis procedure comprises executing a machine learning procedure.

According to some embodiments of the invention the machine learning procedure comprises a supervised learning procedure.

According to some embodiments of the invention the machine learning procedure comprises at least one procedure selected from the group consisting of classification, regression, clustering, support vector machine, linear modeling, k-nearest neighbors analysis, decision tree learning, ensemble learning procedure, neural networks, probabilistic model, graphical model, Bayesian network, and association rule learning.

According to some embodiments of the invention the additional data comprises an at least partial microbiome profile of the individual.

According to some embodiments of the invention the additional data comprises a characteristic intake frequency associated with the food.

According to some embodiments of the invention the additional data comprises an at least partial chemical composition of the food.

According to some embodiments of the invention the additional data comprises an at least a partial blood chemistry of the individual.

According to some embodiments of the invention the additional data comprises an at least a genetic profile of the individual.

According to some embodiments of the invention the additional data comprises a metabolomic data associated with the individual.

According to some embodiments of the invention the additional data comprises a medical condition of the individual.

According to some embodiments of the invention the additional data comprises food intake habits of the individual.

According to some embodiments of the invention the additional data comprises a listing of activities performed by the individual over the time period.

According to some embodiments of the invention the food is a food product.

According to some embodiments of the invention the food is a food type.

According to some embodiments of the invention the food is a family of food types.

According to some embodiments of the invention the food is a combination of a plurality of foods, each food of the plurality of foods being selected from the group consisting of a food product, a food type, and a family of food types.

According to some embodiments of the invention the method, product or apparatus is in use for preventing, controlling and/or treating medical conditions such as conditions that are directly associated with obesity, metabolic syndrome, diabetes and a liver disease or disorder.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

Implementation of the method and/or apparatus of embodiments of the invention can involve performing or completing selected tasks manually, automatically, or a combination thereof. Moreover, according to actual instrumentation and equipment of embodiments of the method and/or apparatus of the invention, several selected tasks could be implemented by hardware, by software or by firmware or by a combination thereof using an operating system.

For example, hardware for performing selected tasks according to embodiments of the invention could be implemented as a chip or a circuit. As software, selected tasks according to embodiments of the invention could be implemented as a plurality of software instructions being executed by a computer using any suitable operating system. In an exemplary embodiment of the invention, one or more tasks according to exemplary embodiments of method and/or apparatus as described herein are performed by a data processor, such as a computing platform for executing a plurality of instructions. Optionally, the data processor includes a volatile memory for storing instructions and/or data and/or a non-volatile storage, for example, a magnetic hard-disk and/or removable media, for storing instructions and/or data. Optionally, a network connection is provided as well. A display and/or a user input device such as a keyboard or mouse are optionally provided as well.

BRIEF DESCRIPTION OF THE SEVERAL VIEWS OF THE DRAWINGS

The patent or application file contains at least one drawing executed in color. Copies of this patent or patent application publication with color drawings will be provided by the Office upon request and payment of the necessary fee.

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

In the drawings:

FIG. 1 is a flowchart diagram of a method suitable for predicting a response of a subject to food, according to some embodiments of the present invention;

FIGS. 2A and 2B are representative illustrations of a subject-specific database (FIG. 2A) and a group database (FIG. 2B) according to some embodiments of the present invention;

FIG. 3 is a flowchart diagram of a method suitable for constructing a database, according to some embodiments of the present invention;

FIG. 4 shows an example of raw blood glucose measurements of a participant in a study performed according to some embodiments of the present invention;

Figure 5A:
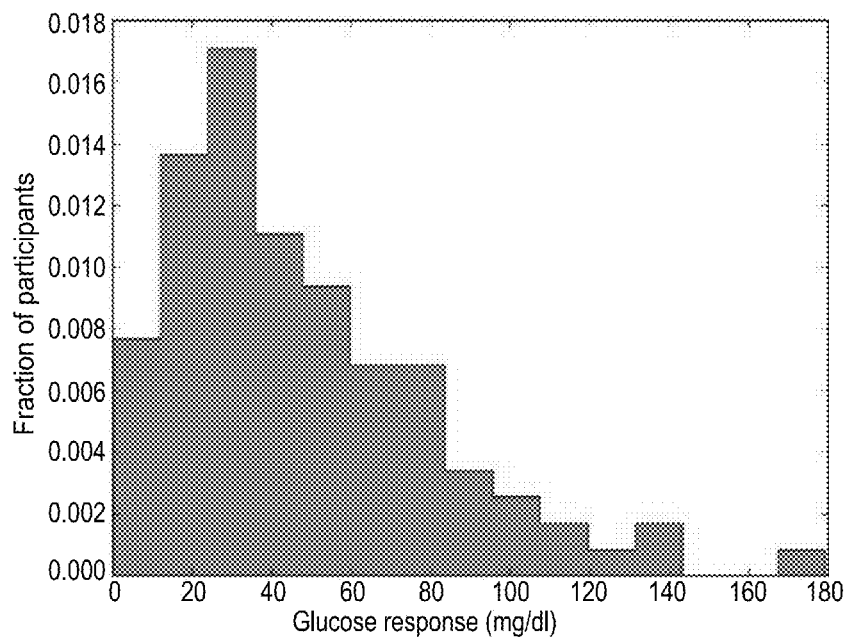
Figure 5B:
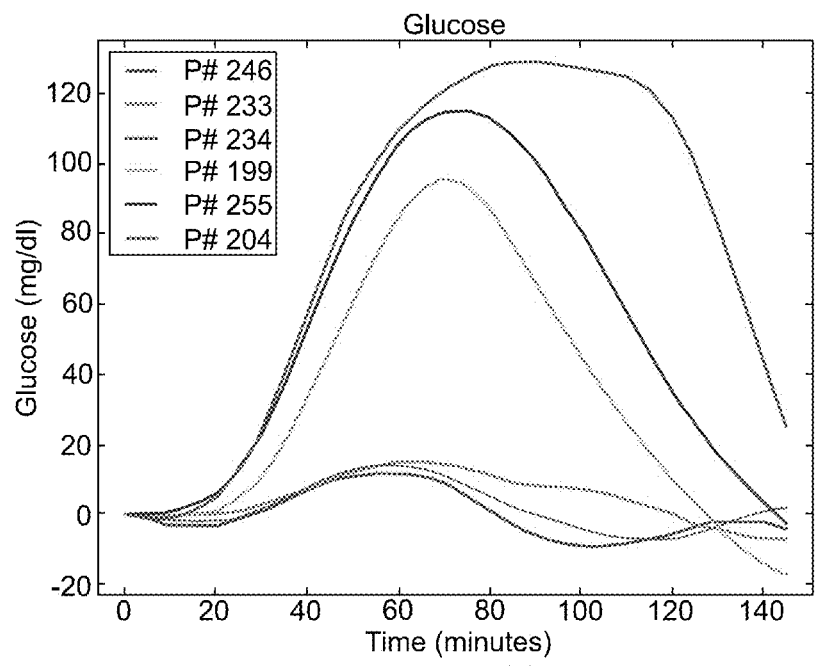
Figure 5C:
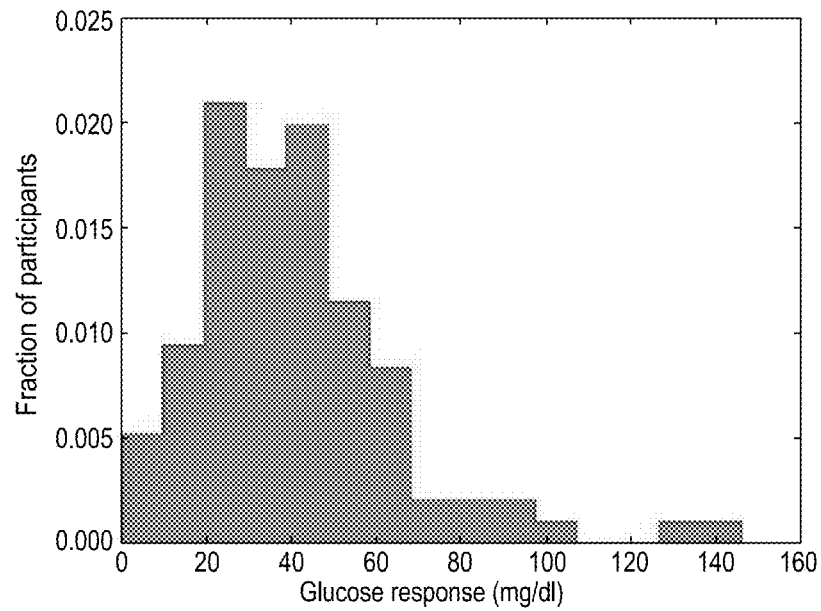
Figure 5D:
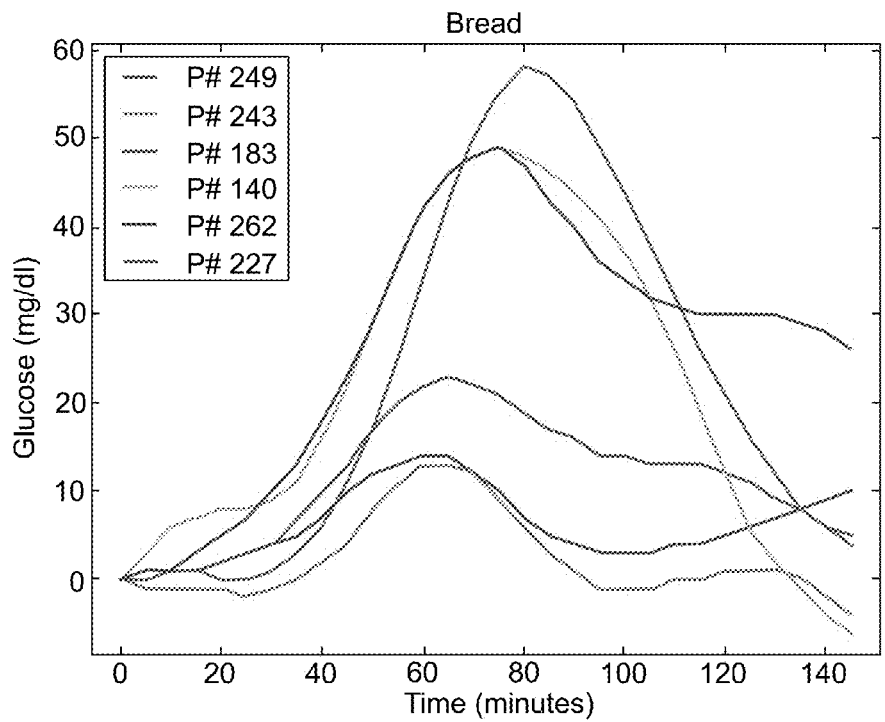
Figure 5E:
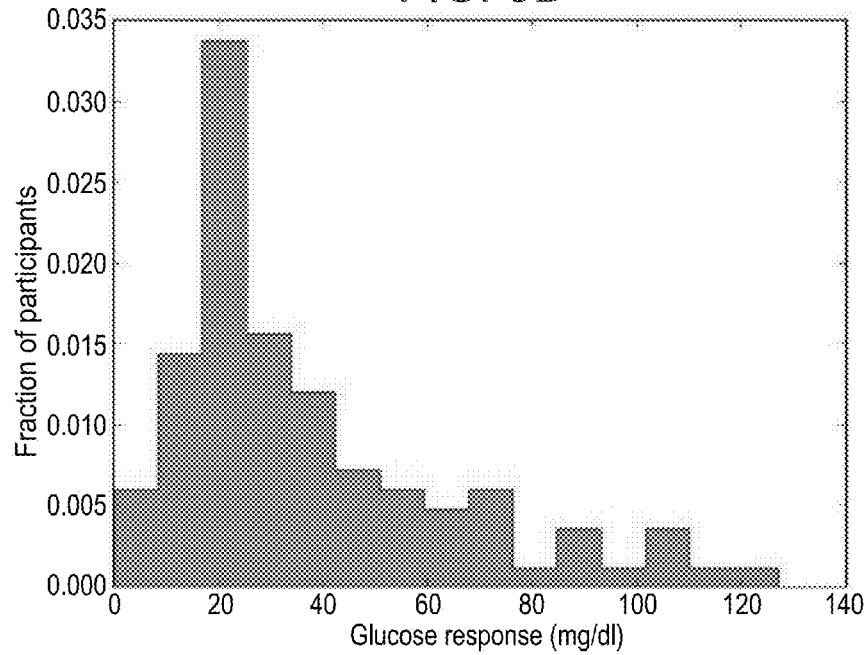
Figure 5F:
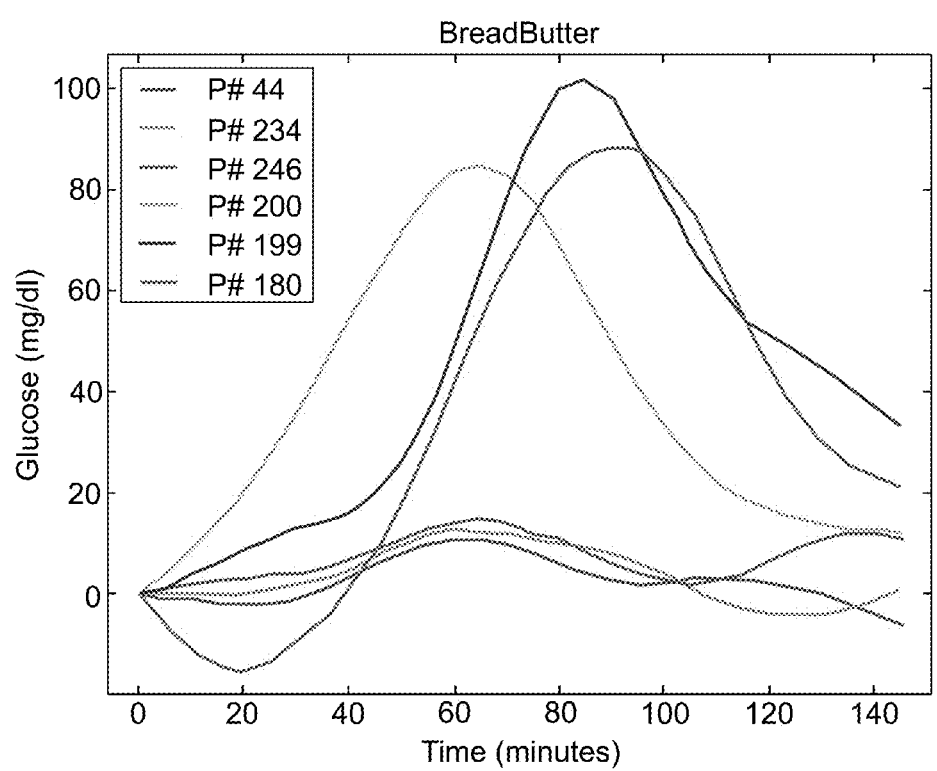
Figure 5G:
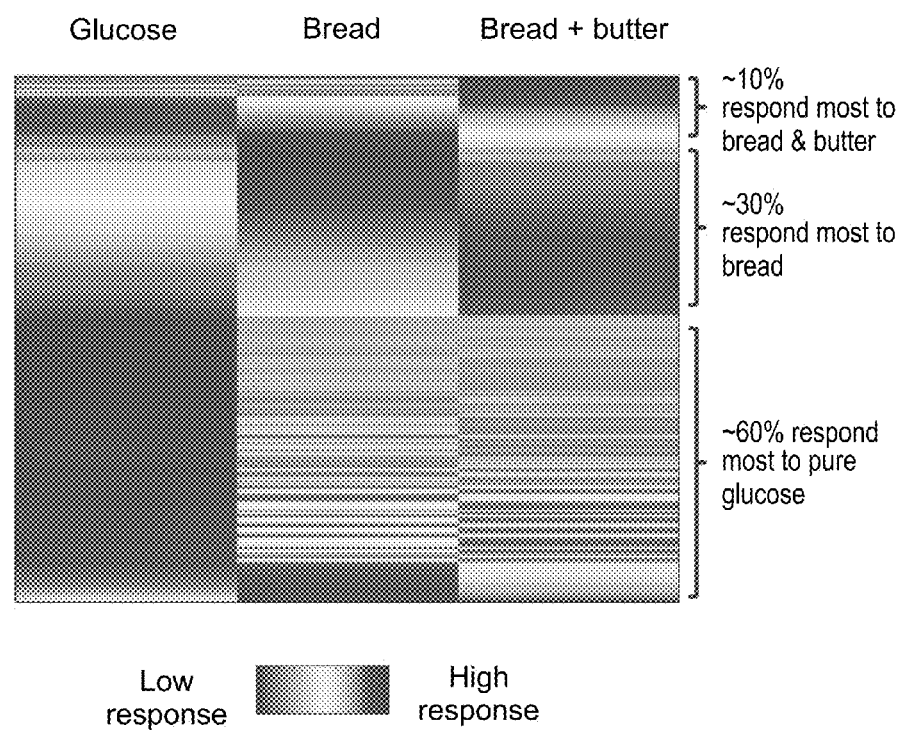
Figure 6A:
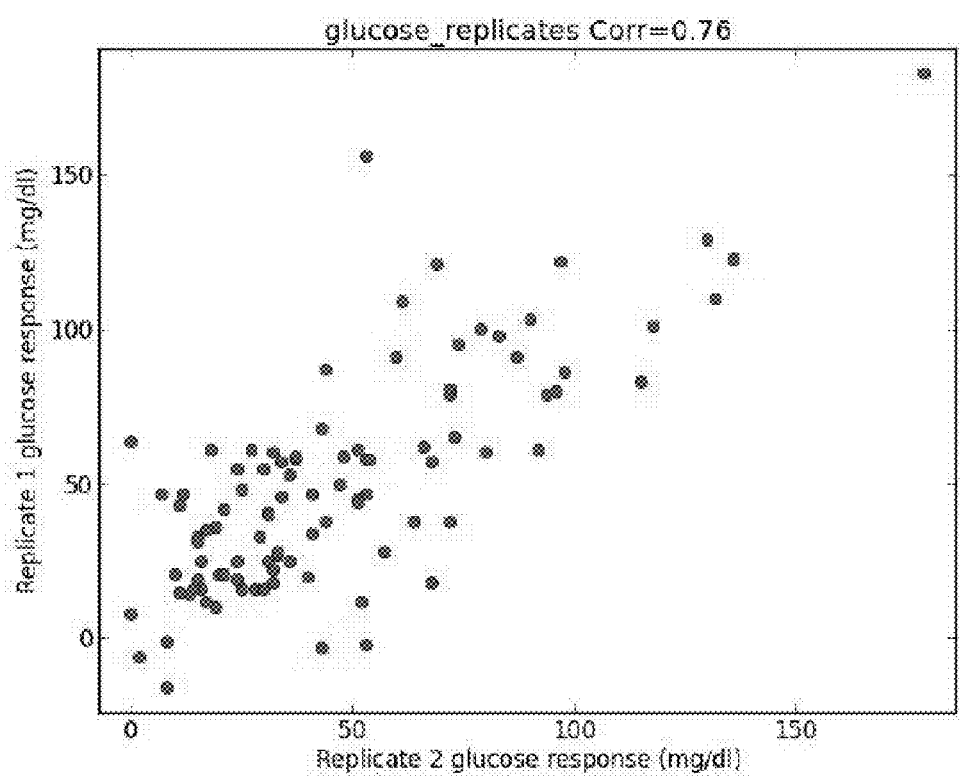
Figure 6B:
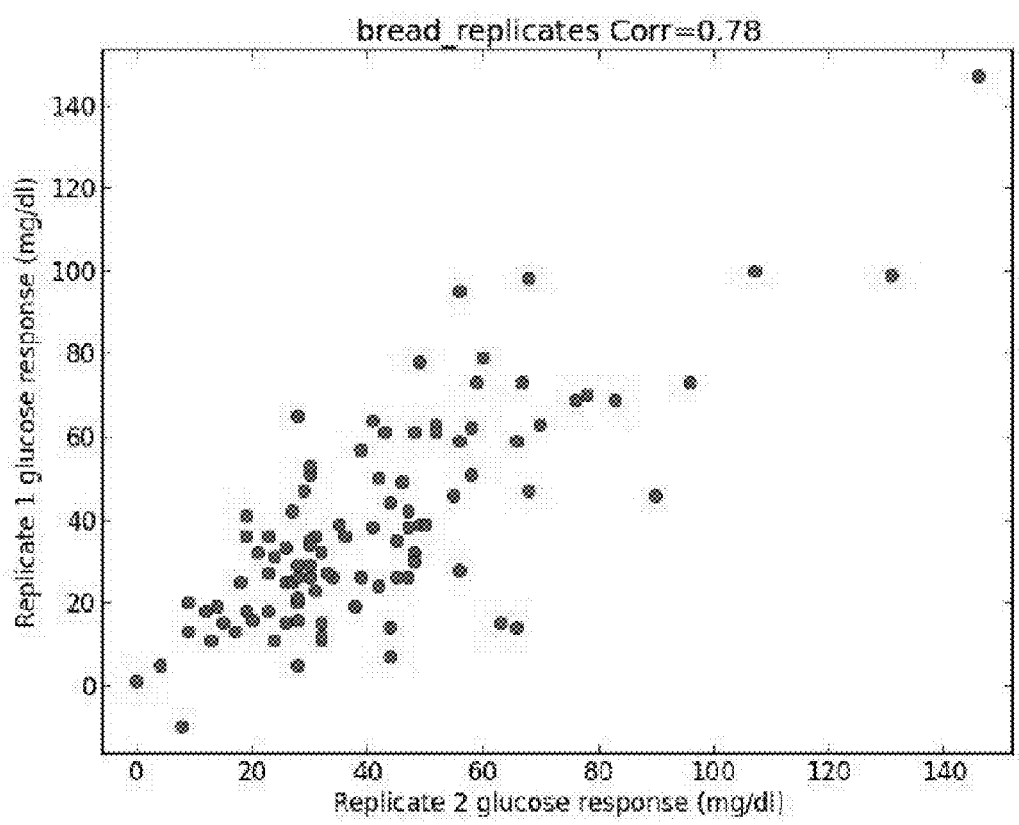
Figure 6C:
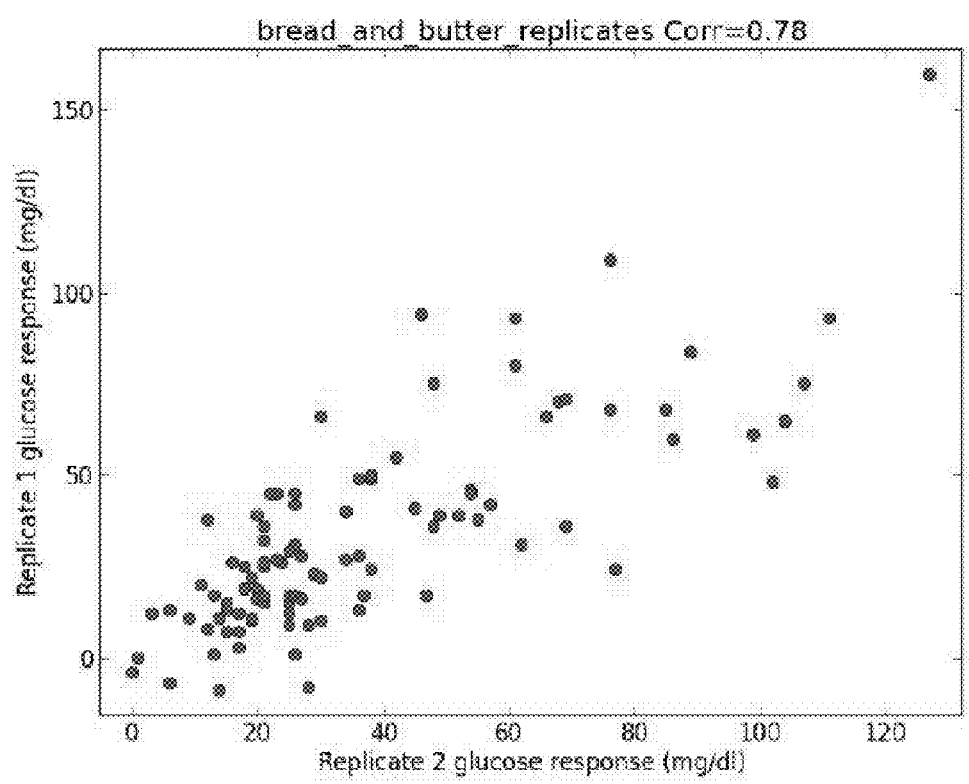
Figure 10A:
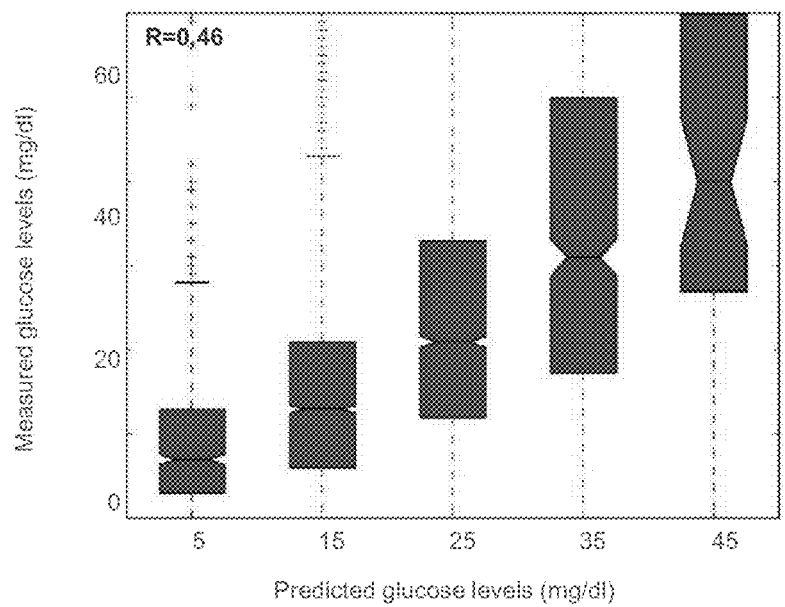
Figure 10B:
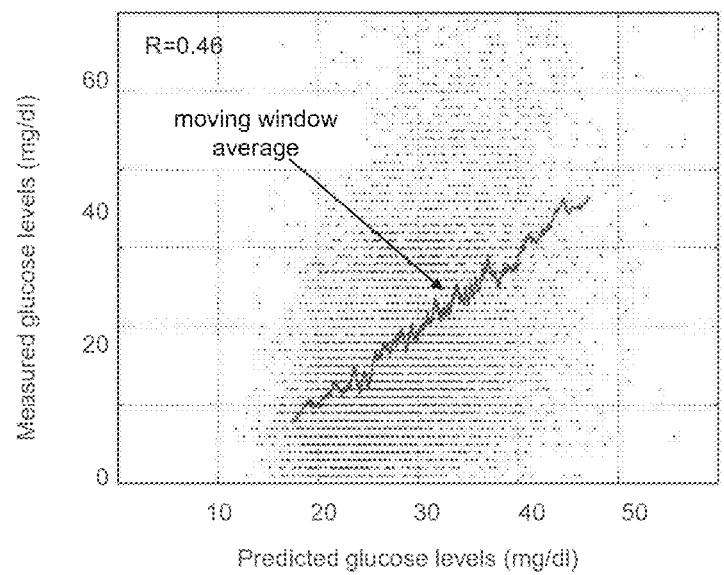

FIGS. 5A-F show histograms of the blood glucose response of participants in a study performed according to some embodiments of the present invention;

FIG. 5G shows clustering of the response of different subjects to glucose, bread, and bread with butter, as measured in experiments performed according to some embodiments of the present invention;

FIGS. 6A-C show comparison of the glucose response of two replicate measurements of Glucose (FIG. 6A), Bread (FIG. 6B) and Bread with butter (FIG. 6C), as obtained during study performed according to some embodiments of the present invention;

FIGS. 7A-E show histograms of the correlation between the amount of carbohydrate in the meal and the glycemic response across the study participants (FIG. 7A), examples of two participants with a low correlation between the amount of carbohydrates and the glycemic response (FIGS. 7B and 7C) and two participants with a high such correlation (FIGS. 7D and 7E), as during study performed according to some embodiments of the present invention;

FIGS. 8A-D show results of glycemic response predictions, as obtained during a study performed according to some embodiments of the present invention;

FIGS. 9A-G show results obtained according to some embodiments of the present invention by analysis which included stochastic gradient boosting using decision trees;

FIGS. 10A-B show predictions of glucose levels obtained according to some embodiments of the present invention using a group database that included responses of other subjects to foods, and a subject-specific database which included data that described the subject but did not include any response to any food.

FIG. 11 is a bar graph illustrating that the average glycemic response in the good week are lower compared to the bad week. Average iAUCmed level of 16 participants in the good (green) and bad (red) weeks. iAUCmed is the incremental area under the curve (AUC) in the first two hours after consuming the meal, relative to the median glucose level 15 minutes before the meal was consumed. The iAUCmed level of a participant is the average iAUCmed of all its breakfasts, lunches and dinners. In the x-axis, IG signifies an impaired glucose participant and H signifies a healthy participant. The first number after the symbol IG/H in the brackets is the average wakeup glucose level of 6 days of experiment and the second number in the brackets is the HbA1C at the beginning of the experiment.

Figure 12:
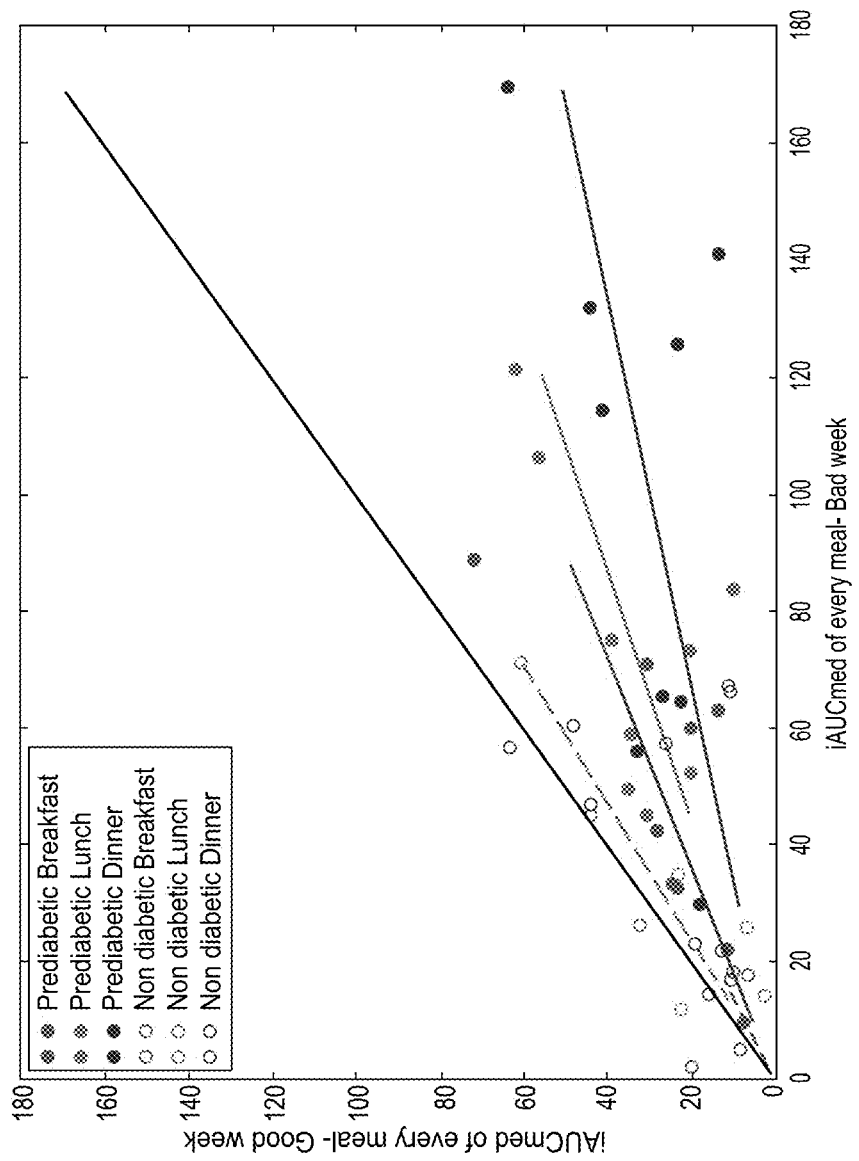

FIG. 12 is a graph illustrating that the glycemic response to meals follows a diurnal pattern, with breakfasts having the lowest response, followed by lunch, and dinner, with the highest. Every dot represents the average iAUCmed of meals in the bad week (x-axis) compared to the good week (y-axis). The majority of points are below the x=y line, meaning that on average AUC in the bad week is higher compared to the good week. Shown are iAUCmed levels of breakfasts (red), lunch (green) and dinner (blue). Filled dots correspond to impaired glucose participants and empty dots correspond to healthy individuals. The slope of the linear fit of all breakfasts in impaired glucose participants (red line) is highest compared to lunch (green line) followed by dinner (green line). Dashed lines correspond to healthy participants and complete lines to glucose impaired participants.

Figure 13A:
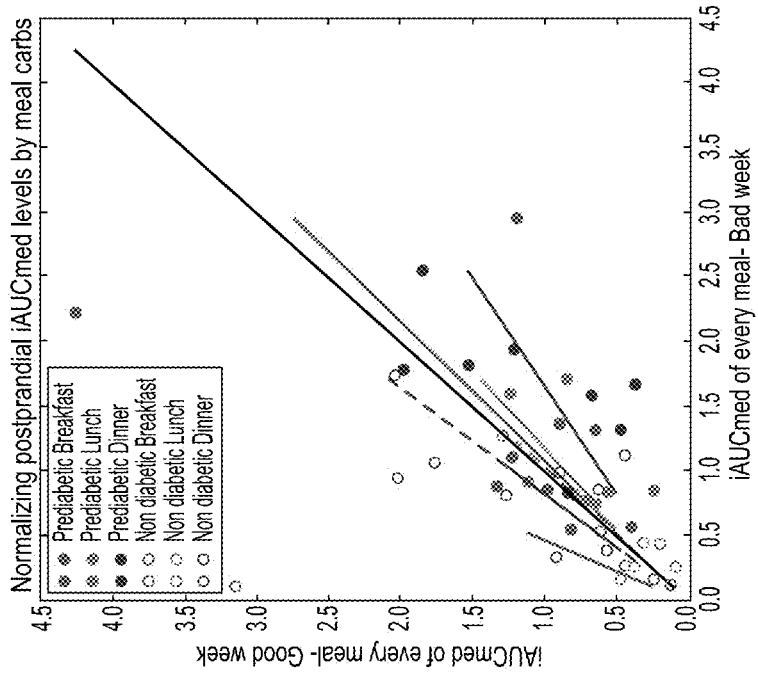
Figure 13B:
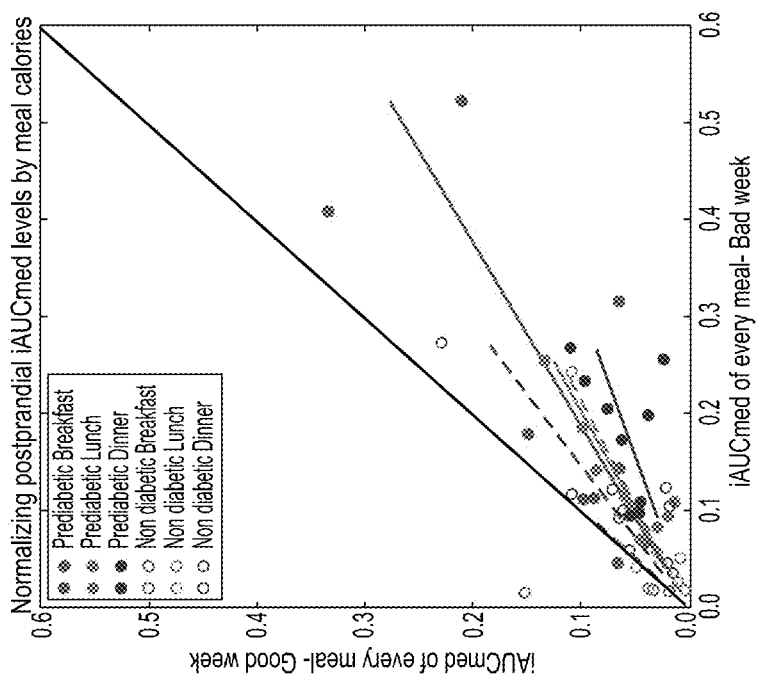

FIGS. 13A-B are graphs illustrating that AUC following meals show a diurnal pattern after normalizing by meal calories and carbohydrate levels. FIG. 13A shows normalize iAUCmed by meal calorie content and FIG. 13B shows normalized iAUCmed by meal carbohydrate content.

DESCRIPTION OF SPECIFIC EMBODIMENTS OF THE INVENTION

The present invention, in some embodiments thereof, relates to nutrition and, more particularly, but not exclusively, to a method and apparatus for predicting a response of a subject to one or more foods.

Before explaining at least one embodiment of the invention in detail, it is to be understood that the invention is not necessarily limited in its application to the details of construction and the arrangement of the components and/or methods set forth in the following description and/or illustrated in the drawings and/or the Examples. The invention is capable of other embodiments or of being practiced or carried out in various ways.

The present embodiments employ computational approach for the purpose of predicting the response of a subject to food, and optionally, but not necessarily, for deciphering the microbiota contribution to this response. The subject whose response to the food is predicted according to some embodiments of the present invention is referred to below as the subject under analysis. The present embodiments preferably exploit previously collected knowledge regarding the responses to foods of a plurality of subjects other than the subject under analysis. This plurality of subjects is referred to below as "other subjects."

In various exemplary embodiments of the invention the predicted response comprise a predicted change in blood sugar level that would occur immediately or shortly after the food is consumed by the subject. The response of a subject to food is optionally and preferably predicted for food to which the response of the subject is unknown. For example, the present embodiments can predict the response of the subject to food which was never consumed by the subject, to food which was taken in the past without determining the response to it, or to a food to which the response of the subject was known in the past but which is suspected to have changed due to a change in the condition (e.g., health condition, growth, microbiome content) of the subject. The present embodiments can predict the response of the subject to food which is known within a particular context of food intake, but is unknown within another context food intake. A context of food intake can include, but is not limited to, an amount of food consumed, time of day at which the food is consumed, time before or after sleep at which the food is consumed, time before or after exercise at which the food is consumed, mental or physiological condition (e.g., stress level, tiredness, mood, ache, posture) of the subject during food intake, environmental condition during food intake (e.g., temperature, place of eating, number of individuals with whom the food is consumed) etc. Thus, for example, for a food for which the response of the subject is known in the morning, the present embodiments can predict the response of the subject to food at noon time or after.

In some embodiments of the present invention the food is a food product (e.g., a specific food product marketed as such by a specific manufacturer, or by two or more manufacturers manufacturing the same food product). In some embodiments of the present invention the food is a food type (e.g., a food which exhibit different modifications, for example, white rice, that may have different species, all of which are referred to as "white rice", or whole wheat bread that may be backed from various mixtures, etc). In some embodiments of the present invention the food is a family of food types. The family can be categorized according to the main ingredient of the food type, for example, sweets, dairies, fruits, herbs, vegetables, fish, meet, etc. In some embodiments of the present invention the family of food types is a food group, such as, but not limited to, carbohydrates, which is a family encompassing food types rich in carbohydrates, proteins, which is a family encompassing food types rich in protein, and fats, which is a family encompassing food types rich in fats, minerals which is a family encompassing food types rich in minerals, vitamins which is a family encompassing food types rich in vitamins, etc. In some embodiments of the present invention the food is a food combination which comprises a plurality of different food products, and/or different food types and/or different food families. Such a combination is referred to as "a complex meal." The complex meal can be provided as a list of the food products, food types and/or families of food types that form the combination. The list may or may not include the particular amount of each food product, food type and/or family of food types in the combination.

Any of the methods described herein can be embodied in many forms. For example, it can be embodied in on a tangible medium such as a computer for performing the method operations. It can be embodied on a computer readable medium, comprising computer readable instructions for carrying out the method operations. It can also be embodied in electronic device having digital computer capabilities arranged to run the computer program on the tangible medium or execute the instruction on a computer readable medium.

Computer programs implementing the method of the present embodiments can commonly be distributed to users on a distribution medium such as, but not limited to, CD-ROMs or flash memory media. From the distribution medium, the computer programs can be copied to a hard disk or a similar intermediate storage medium. In some embodiments of the present invention, computer programs implementing the method of the present embodiments can be distributed to users by allowing the user to download the programs from a remote location, via a communication network, e.g., the internet. The computer programs can be run by loading the computer instructions either from their distribution medium or their intermediate storage medium into the execution memory of the computer, configuring the computer to act in accordance with the method of this invention. All these operations are well-known to those skilled in the art of computer systems.

Figure 1:
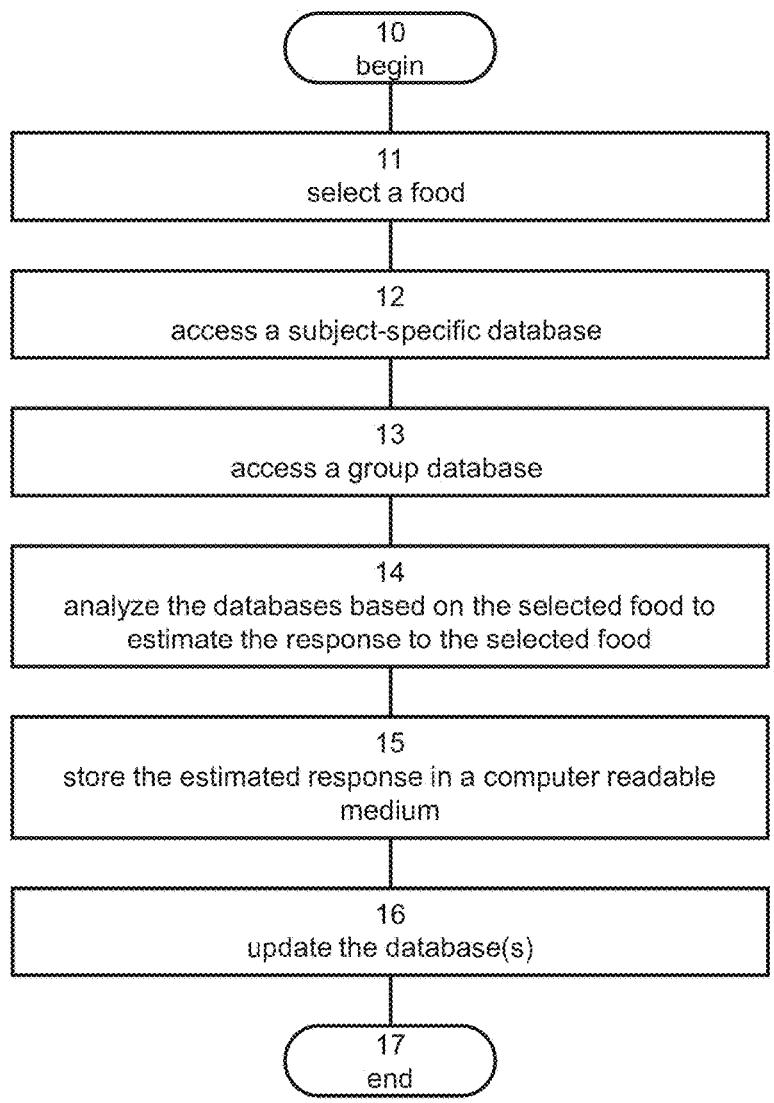

Referring now to the drawings, FIG. 1 is a flowchart diagram of a method suitable for predicting a response of a subject to food, according to some embodiments of the present invention. It is to be understood that, unless otherwise defined, the operations described hereinbelow can be executed either contemporaneously or sequentially in many combinations or orders of execution. Specifically, the ordering of the flowchart diagrams is not to be considered as limiting. For example, two or more operations, appearing in the following description or in the flowchart diagrams in a particular order, can be executed in a different order (e.g., a reverse order) or substantially contemporaneously. Additionally, several operations described below are optional and may not be executed.

The method begins at 10 and continues to 11 at which a food to which a response of the subject is unknown is selected. The food product can be selected from a list of foods that can be provided to the subject or another user by means of, for example, a user interface device or assembly, such as a touch screen or a display device and a keyboard. Optionally, a list of main food type families can be presented to the user for selection. Upon selection of a family of food types, a list of food types that belong to that family can optionally be provided for selection, if desired. Upon selection of a food type, a list of food products can optionally be provided from which the user can select the food, if desired. Also contemplated are embodiments in which the subject or another user types the food using a keyboard. Optionally, a completion algorithm (e.g., word-completion) is employed while the user is typing, as known in the art. The selection of food can optionally and preferably be accompanied with a selection of a context of food intake for the selected food. For example, a list of contexts of food intake can be presented to the user for selection.

The method continues to 12 at which a subject-specific database is accessed. The subject-specific database is stored in a computer readable format on a computer readable medium, and is optionally and preferably accessed by a data processor, such as a general purpose computer or dedicated circuitry.

The subject-specific database comprises data describing the subject. In some embodiments of the present invention the subject-specific database comprises data pertaining to responses of the subject to foods. A representative illustration of a subject-specific database 22 according to some embodiments of the present invention is provided in FIG. 2A.

The data of the subject-specific database can be arranged to form a set of responses of the subject to a respective set of foods. The number of foods in the subject-specific database is preferably at least 10 or at least 20 or at least 30 or more. When the foods and responses are defined as sets, the number of foods can be defined as the sizes of the sets (the number of elements in each set).

In various exemplary embodiments of the invention the subject-specific database includes data pertaining to responses of the subject to foods, but does not include a response of the subject to the selected food. In other words, in these embodiments, none of the foods in the set of set of foods is the food that is selected at 11. Foods that have some similarity to the selected food may exist in the subject-specific database. If, for example, a food product is selected, then the subject-specific database preferably does not include this specific food product, but may optionally and preferably include a food product that belongs to the same type or the same family of types as the selected food product. If, for example, a food type is selected, then the subject-specific database preferably does not include this food type, but may optionally and preferably include a food type that belongs to the same family of types as the selected food type. In embodiments in which a context of food intake is also selected, the subject-specific database may optionally include a response of the subject to the selected food, but preferably in a context other than the selected context.

While the above embodiments are described with a particular emphasis to subject-specific database includes data pertaining to responses of the subject to foods, it is to be understood that the subject-specific database may be devoid of any response of the subject to foods. The subject-specific database can include any data that describes the subject. Representative examples of types of data other than responses to foods include, without limitation, a microbiome profile, a partial microbiome profile, blood chemistry of the subject, partial blood chemistry of the subject, genetic profile of the subject, metabolomic data associated with the subject, the medical condition of the subject, food intake habits of the subject, and the like. These and other types of data are described in more detail below.

The method continues to 13 at which a group database is accessed. The group database is stored in a computer readable format on a computer readable medium, and is optionally and preferably accessed by a data processor, such as a general purpose computer or dedicated circuitry. Both databases can be stored on the same medium and are optionally and preferably accessed by the same data processor.

A representative illustration of a group database 24 according to some embodiments of the present invention is provided in FIG. 2B. The group database comprises data pertaining to responses of other subjects to foods. However, unlike the subject-specific database which may, optionally, includes only responses of the subject under analysis to foods, the responses of the group database includes responses of other subjects to foods. The data of the group database can be arranged to form a set of responses to a respective set of foods.

In the subject-specific database illustrated in FIG. 2A, each entry can be described as a tuple (F, R) where F represents a particular food in the database and R represents the subject's response to F. Thus, the exemplified illustration is of a two-dimensional database in which all the elements can be described by a vector in a two-dimensional space spanned by the foods and respective responses. In the group database illustrated in FIG. 2B, each entry can be described as a tuple (S, F, R) where S represent a particular subject in the group database, F represents a particular food and R represents the response of subject S to food F. Thus, the exemplified illustration is of a three-dimensional database in which all the elements can be described by a vector in a three-dimensional space spanned by the subjects, foods and respective responses. Some embodiments of the present invention contemplate use of databases of higher dimensions. Such databases are described hereinafter.

The group database may optionally and preferably also include one or more of, more preferably all, the entries of the subject-specific database. In embodiments in which group database includes all the entries of the subject-specific database, it is not necessary to use two separate databases, since the entire dataset is contained in one inclusive database. Yet, such an inclusive database is optionally and preferably annotated in a manner that allows distinguishing between the portion of the inclusive database that is associated with the subject under analysis, and the portion of the inclusive database that is associated only with the other subjects. In the context of the present disclosure, the portion of the inclusive database that is associated with the subject under analysis is referred to as the subject-specific database even when it is not provided as a separate database. Similarly, the portion of the inclusive database that is associated only with the other subjects is referred to as the group database even when it is not provided as a separate database.

In some embodiments of the invention the group database includes the food selected at 11, and a response of one or more other subjects to the selected food, but not the response of the subject under analysis to the selected food. Thus, in some embodiments of the present invention, the response of the subject under analysis to the food selected at 11 is not present in the subject-specific database and is also not present in the group database.

The group database preferably includes responses of many subjects (e.g., at least 10 subjects or at least 100 subjects, e.g., 500 subjects or more) to foods. The number of different foods in the group database is optionally and preferably larger than the number of different foods in the subject-specific database. Both databases may include the same number of different food types and/or different families of food type families. However, this need not necessarily be the case, since, the number of different food types and/or the number of different families of food types may differ among the two databases.

Since the group database comprises data pertaining to a plurality of subjects, the set of foods in this database may include repeating elements. For example, consider, for simplicity, three subjects denoted $S_1$, $S_2$ and $S_3$, and four foods denoted $F_1$, $F_2$, $F_3$ and $F_4$. Suppose that the group database includes data pertaining to these subjects and these foods, wherein the group database includes the responses of each subjects $S_1$ and $S_2$ to all four foods, and the responses of subject $S_3$ to foods $F_1$, $F_2$ and $F_3$, but not $F_4$ (note that without lose of generality this is consistent with a situation in which $S_3$ is the subject under analysis and $F_4$ is the selected food). In this example, each of the foods $F_1$, $F_2$ and $F_3$ may appear three times in the group database and food $F_4$ may appear two times in the group database. Mathematically, denoting the response of the ith subject to the jth food by $R_{ij}$, the set of responses of the group database can be $\{R_{11}, R_{12}, R_{13}, R_{14}, R_{21}, R_{22}, R_{23}, R_{24}, R_{31}, R_{32}, R_{33}\}$ and the set of foods of the group database can be $\{F_1, F_2, F_3, F_4, F_1, F_2, F_3, F_4, F_1, F_2, F_3\}$.

It is to be understood that while the databases described herein may be arranged as sets, other types of data structures are also contemplated in some embodiments of the invention. Yet, at least some of the data in the databases are arrangeable into sets as exemplified above.

Once the databases are accessed the method continues to 14 at which the databases are analyzed based on the selected food to estimate the response of the subject to the selected food. The analysis can be executed in more than one way. Exemplified techniques suitable for analyzing the databases according to some embodiments of the present invention are provided hereinunder.

The method optionally and preferably continues to 15 at which the estimated response is stored, at least temporarily, in a computer readable medium from which it can be extracted or displayed as desired. In some embodiments, the method continues to 16 at which one or both the databases is/are updated using the estimated response.

The method ends at 17.

Before providing a further detailed description of the method for predicting a response of a subject to food, as delineated hereinabove and in accordance with some embodiments of the present invention, attention will be given to the advantages and potential applications offered thereby.

The present inventors demonstrated the ability of the method of the present embodiments to provide personal predictions of a subject's response (e.g. glucose, cholesterol, sodium, potassium, calcium) that are tailored to the various collected parameters of the subject. The present embodiments thus provide a personally-based nutrition which is a significant improvement to the conventional empirically-based nutrition. The present embodiments can be used as means of primary prevention or reducing the risk of, for example, hyperglycemia in normal and susceptible individuals. The present embodiments provide biological and computational toolbox that incorporates the dietary habits and optionally also the genetics and/or microbiota of the subject in predicting his/her responses (e.g. glycemic response) to a variety of untested foods.

The present embodiments are useful for providing individualize prediction of subject-specific dietary interventions, for example, for the purpose of primary and/or secondary prevention and/or treatment and/or control of medical conditions such as conditions that are directly associated with obesity, metabolic syndrome, diabetes and a liver disease or disorder.

In general, the terms "prevent," "control" and "treat" encompass the prevention of the development of a disease or a symptom from a subject who may have a predisposition of the disease or the symptom but has yet been diagnosed to have the disease or the symptom; the inhibition of the symptoms of a disease, namely, inhibition or retardation of the progression thereof; and the alleviation of the symptoms of a disease, namely, regression of the disease or the symptoms, or inversion of the progression of the symptoms.

All types of obesity may be controlled or treated in accordance with some embodiments of the invention, including, without limitation, endogenous obesity, exogenous obesity, hyperinsulinar obesity, hyperplastic-hypertrophic obesity, hypertrophic obesity, hypothyroid obesity and morbid obesity. For example, the present embodiments can be used to slow down, stop or reverse body weight gain, specifically body fat gain, resulting in a maintenance or decrease in body weight. A decrease in weight or body fat may protect against cardiovascular disease by lowering blood pressure, total cholesterol, LDL cholesterol and triglycerides, and may alleviate symptoms associated with chronic conditions such as hypertension, coronary heart disease, type 2 diabetes, hyperlipidemia, osteoarthritis, sleep apnea and degenerative joint disease.

Metabolic syndrome, or Syndrome X, is a complex multifactorial condition accompanied by an assortment of abnormalities including hypertension, hypertriglyceridemia, hyperglycemia, low levels of HDL-C, and abdominal obesity. Individuals with these characteristics typically manifest a prothrombotic and pro-inflammatory state. Available data suggest that metabolic syndrome is truly a syndrome (a grouping of risk factors).

According to the World Health Organization (WHO) Guideline, metabolic syndrome is present if an individual manifests: a) hypertension (>140 mm Hg systolic or >90 mm Hg diastolic); b) dyslipidemia, defined as elevated plasma triglycerides (150 mg/dL), and/or low high-density lipoprotein (HDL) cholesterol (<35 mg/dL in men, <39 mg/dL in women); c) visceral obesity, defined as a high body mass index (BMI) (30 kg/m2) and/or a high waist-to-hip ratio (>0.90 in men, >0.85 in women); and d) microalbuminuria (urinary albumin excretion rate of 20 g/min) See WHO-International Society of Hypertension Guidelines for the Management of Hypertension. Guidelines Subcommittee. J. Hypertens. 17:151-183, 1999.

According to the National Cholesterol Education Program (NCEP ATP III study) metabolic syndrome is diagnosed if three (3) or more of the following five (5) risk factors are present: 1) a waist circumference >102 cm (40 in) for men or >88 cm (37 in) for women; 2) a triglyceride level of 150 mg/dL; 3) an HDL cholesterol level <40 mg/dL for men or <50 mg/dL for women; 4) blood pressure >130/85 mm Hg; or 5) a fasting glucose >110 mg/dL. JAMA 285: 2486-2497, 2001.

Each of the disorders associated with metabolic syndrome are risk factors in their own right, and can promote atherosclerosis, cardiovascular disease, stroke, systemic micro and macro vascular complications and other adverse health consequences. However, when present together, these factors are predictive of increased risk of cardiovascular disease, stroke and systemic micro and macro vascular complications.

The present embodiments can reduce, in severity and/or in number, the symptoms of the metabolic syndrome, when shown in the subject under analysis. Such symptoms may include elevated blood glucose, glucose intolerance, insulin resistance, elevated triglycerides, elevated LDL-cholesterol, low high-density lipoprotein (HDL) cholesterol, elevated blood pressure, abdominal obesity, pro-inflammatory states, and pro-thrombotic states. The present embodiments can also reduce the risk of developing associated diseases, and/or delay the onset of such diseases. Such associated diseases include cardiovascular disease, coronary heart disease and other diseases related to plaquing of the artery walls and diabetic conditions.

Diabetic conditions include, for example, type 1 diabetes, type 2 diabetes, gestational diabetes, pre-diabetes, slow onset autoimmune diabetes type 1 (LADA), hyperglycemia, and metabolic syndrome. The diabetes may be overt, diagnosed diabetes, e.g., type 2 diabetes, or a pre-diabetic condition.

Diabetes mellitus (generally referred to herein as "diabetes") is a disease that is characterized by impaired glucose regulation. Diabetes is a chronic disease that occurs when the pancreas fails to produce enough insulin or when the body cannot effectively use the insulin that is produced, resulting in an increased concentration of glucose in the blood (hyperglycemia). Diabetes may be classified as type 1 diabetes (insulin-dependent, juvenile, or childhood-onset diabetes), type 2 diabetes (non-insulin-dependent or adult-onset diabetes), LADA diabetes (late autoimmune diabetes of adulthood) or gestational diabetes. Additionally, intermediate conditions such as impaired glucose tolerance and impaired fasting glycemia are recognized as conditions that indicate a high risk of progressing to type 2 diabetes.

In type 1 diabetes, insulin production is absent due to autoimmune destruction of pancreatic beta-cells. There are several markers of this autoimmune destruction, detectable in body fluids and tissues, including islet cell autoantibodies, insulin autoantibodies, glutamic acid decarboxylase autoantibodies, and tyrosine phosphatase ICA512/IA-2 autoantibodies. In type 2 diabetes, comprising 90% of diabetics worldwide, insulin secretion may be inadequate, but peripheral insulin resistance is believed to be the primary defect. Type 2 diabetes is commonly, although not always, associated with obesity, a cause of insulin resistance.

Type 2 diabetes is often preceded by pre-diabetes, in which blood glucose levels are higher than normal but not yet high enough to be diagnosed as diabetes.

The term "pre-diabetes," as used herein, is interchangeable with the terms "Impaired Glucose Tolerance" or "Impaired Fasting Glucose," which are terms that refer to tests used to measure blood glucose levels.

Chronic hyperglycemia in diabetes is associated with multiple, primarily vascular complications affecting microvasculature and/or macrovasculature. These long-term complications include retinopathy (leading to focal blurring, retinal detachment, and partial or total loss of vision), nephropathy (leading to renal failure), neuropathy (leading to pain, numbness, and loss of sensation in limbs, and potentially resulting in foot ulceration and/or amputation), cardiomyopathy (leading to heart failure), and increased risk of infection. Type 2, or noninsulin-dependent diabetes mellitus (NIDDM), is associated with resistance of glucose-utilizing tissues like adipose tissue, muscle, and liver, to the physiological actions of insulin. Chronically elevated blood glucose associated with NIDDM can lead to debilitating complications including nephropathy, often necessitating dialysis or renal transplant; peripheral neuropathy; retinopathy leading to blindness; ulceration and necrosis of the lower limbs, leading to amputation; fatty liver disease, which may progress to cirrhosis; and susceptibility to coronary artery disease and myocardial infarction. The present embodiments can be used to reduce the risk of developing of diabetes or to delay the onset of the disease. The present embodiments can be used to reduce the risk of developing associated complications and/or delay the onset of such complications.

Diabetic conditions can be diagnosed or monitored using any of a number of assays known in the field. Examples of assays for diagnosing or categorizing an individual as diabetic or pre-diabetic or monitoring said individual include, but are not limited to, a glycosylated hemoglobin (HbA1c) test, a connecting peptide (C-peptide) test, a fasting plasma glucose (FPG) test, an oral glucose tolerance test (OGTT), and a casual plasma glucose test.

HbA1c is a biomarker that measures the amount of glycosylated hemoglobin in the blood. HbA1c designates a stable minor glycated sub fraction of hemoglobin. It is a reflection of the mean blood glucose levels during the last 6-8 weeks, and is expressed in percent (%) of total hemoglobin. Alternatively, diabetes or pre-diabetes can be diagnosed by measuring blood glucose levels, for example, using a glucose monitor, or any of several tests known in the field, including, without limitation, a fasting plasma glucose test or an oral glucose tolerance test. Using the fasting plasma glucose (FPG) test, a patient is classified as diabetic, if the patient has a threshold FPG greater than 125 mg/dl, and a patient is classified as pre-diabetic if the patient has a threshold FPG greater than 100 mg/dl but less than or equal to 125 mg/dl. Using the oral glucose tolerance test (OGTT), a patient is classified as diabetic if the patient has a threshold 2-hour OGTT glucose level greater than 200 mg/dl. A patient is classified as pre-diabetic if the patient has a threshold 2-hour OGTT glucose level greater than 140 mg/dl but less than 200 mg/dl.

C-peptide, produced from proinsulin molecules, is secreted from islet cells into the bloodstream in equimolar proportion as insulin, and is used a biomarker for beta-cell function and insulin secretion. A fasting C-peptide measurement greater than 2.0 ng/ml is indicative of high levels of insulin, while a fasting C-peptide measurement less than 0.5 ng/ml indicates insufficient insulin production.

A subject who has been classified as having a diabetic condition, and who is analyzed according to some embodiments of the present invention, may be monitored for efficacy of treatment by measuring blood glucose, e.g., using a blood glucose monitor and/or by measuring biomarkers indicators, including but not limited to, glycosylated hemoglobin levels, C-peptide levels, fasting plasma glucose levels, and oral glucose tolerance test (OGTT) levels.

Some embodiments of the present invention can be used to prevent, treat and/or control hyperlipidemia (also referred to as hyperlipoproteinemia, or hyperlipidaemia) which involves abnormally elevated levels of any or all lipids and/or lipoproteins in the blood. It is the most common form of dyslipidemia (which includes any abnormal lipid levels). Hyperlipidemias are also classified according to which types of lipids are elevated, that is hypercholesterolemia, hypertriglyceridemia or both in combined hyperlipidemia. Elevated levels of Lipoprotein(a) are also classified as a form of hyperlipidemia. Under the terms include are also, hyperlipoproteinemia Type I, hyperlipoproteinemia Type II, hyperlipoproteinemia Type III, hyperlipoproteinemia Type IV and hyperlipoproteinemia Type V. As well as unclassified familial forms and acquired forms of hyperlipidemia.

Some embodiments of the present invention can be used to prevent, treat and/or control liver diseases and disorders including hepatitis, cirrhosis, non-alcoholic steatohepatitis (NASH) (also known as non-alcoholic fatty liver disease-NAFLD), hepatotoxicity and chronic liver disease.

The term "liver disease" applies to many diseases and disorders that cause the liver to function improperly or to cease functioning, and this loss of liver function is indicative of liver disease. Thus, liver function tests are frequently used to diagnose liver disease. Examples of such tests include, but are not limited to, the following: (1) Assays to determine the levels of serum enzymes such as lactate dehydrogenase (LDH), alkaline phosphatase (ALP), aspartate aminotransferase (AST), and alanine aminotransferase (ALT), where an increase in enzyme levels indicates liver disease. One of skill in the art will reasonably understand that these enzyme assays indicate only that the liver has been damaged. They do not assess the liver's ability to function. Other tests can be used to assay a liver's ability to function; (2) Assays to determine serum bilirubin levels. Serum bilirubin levels are reported as total bilirubin and direct bilirubin. Normal values of total serum bilirubin are 0.1-1.0 mg/dl (e.g., about 2-18 mmol/L). Normal values of direct bilirubin are 0.0-0.2 mg/dl (0-4 mmol/L). Increases in serum bilirubin are indicative of liver disease. (3) Assays to determine serum protein levels, for example, albumin and the globulins (e.g., alpha, beta, gamma). Normal values for total serum proteins are 6.0-8.0 g/dl (60-80 g/L). A decrease in serum albumin is indicative of liver disease. An increase in globulin is indicative of liver disease.

Other tests include prothrombin time, international normalized ratio, activated clotting time (ACT), partial thromboplastin time (PTT), prothrombin consumption time (PCT), fibrinogen, coagulation factors; alpha-fetoprotein, and alpha-fetoprotein-L3 (percent).

One type of liver disease is hepatitis. Hepatitis is an inflammation of the liver that can be caused by viruses (e.g., hepatitis virus A, B and C (HAV, HBV, and HCV, respectively), chemicals, drugs, alcohol, inherited diseases, or the patient's own immune system (autoimmune hepatitis). This inflammation can be acute and resolve within a few weeks to months, or chronic, and persist over many years. Chronic hepatitis can persist for decades before causing significant symptoms, such as cirrhosis (scarring and loss of function), liver cancer, or death. Other examples of the different diseases and disorders encompassed by the term "liver disease" and suitable for treatment or prevention or control according to some embodiments of the present invention, but are not limited to amebic liver abscess, biliary atresia, fibrosis, cirrhosis, coccidioidomycosis, delta agent, hepatocellular carcinoma (HCC), alcoholic liver disease, primary biliary cirrhosis, pyogenic liver abscess, Reye's syndrome, sclerosing cholangitis, and Wilson's disease. Some embodiments of the present invention are useful for the treatment of liver disease characterized by the loss or damage of parenchymal liver cells. In some aspects, the etiology of this can be a local or systemic inflammatory response.

Liver failure occurs when large parts of the liver become damaged and the liver is no longer able to perform its normal physiological function. In some aspects, liver failure can be diagnosed using the above described assays of liver function or by a subject's symptoms. Symptoms that are associated with liver failure include, for example, one or more of the following, nausea, loss of appetite, fatigue, diarrhea, jaundice, abnormal/excessive bleeding (e.g., coagulopathy), swollen abdomen, mental disorientation or confusion (e.g., hepatic encephalopathy), sleepiness, and coma.

Chronic liver failure occurs over months to years and is most commonly caused by viruses (e.g., HBV and HCV), long-term/excessive alcohol consumption, cirrhosis, hemochromatosis, and malnutrition. Acute liver failure is the appearance of severe complications after the first signs of liver disease (e.g., jaundice) and includes a number of conditions, all of which involve severe hepatocyte injury or necrosis. Some embodiments of the present invention are useful for the treatment of hyperacute, acute, and subacute liver failure, fulminant hepatic failure and late onset fulminant hepatic failure, all of which are referred to herein as "acute liver failure." Common causes for acute liver failure include, for example, viral hepatitis, exposure to certain drugs and toxins (e.g., fluorinated hydrocarbons) (e.g., trichloroethylene and tetrachloroethane), amanita phalloides (e.g., commonly found in the "death-cap mushroom"), acetaminophen (paracetamol), halothanes, sulfonamides, henytoins), cardiac-related hepatic ischemia (e.g., myocardial infarction, cardiac arrest, cardiomyopathy, and pulmonary embolism), renal failure, occlusion of hepatic venous outflow (e.g., Budd-Chiari syndrome), Wilson's disease, acute fatty liver of pregnancy, amebic abscesses, and disseminated tuberculosis.

The term "hepatitis" is used to describe a liver condition which implies injury to the liver characterized by the presence of inflammatory cells in the tissue of the organ. The condition can be self-limiting, healing on its own, or can progress to scarring of the liver. Hepatitis is acute when it lasts less than six months and chronic when it persists longer than six months. A group of viruses known as the hepatitis viruses cause most cases of liver damage worldwide. Hepatitis can also be due to toxins (notably alcohol), other infections or from autoimmune process. Hepatitis includes hepatitis from viral infections, including Hepatitis A through E (A, B, C, D and E—more than 95% of viral cause), Herpes simplex, Cytomegalovirus, Epstein-Barr virus, yellow fever virus, adenoviruses; non-viral infections, including toxoplasma, Leptospira, Q fever, rocky mountain spotted fever, alcohol, toxins, including amanita toxin in mushrooms, carbon tetrachloride, asafetida, among others, drugs, including paracetamol, amoxycillin, antituberculosis medicines, minocycline and numerous others as described herein; ischemic hepatitis (circulatory insufficiency); pregnancy; autoimmune conditions, including Systemic Lupus Erythematosus (SLE); and non-alcoholic steatohepatitis.

"Sterile inflammation" is used to describe inflammation of the liver which is triggered by intracellular molecules released from dying cells that have lost integrity of their plasma membrane. This inflammation occurs in the absence of causative agents such as viruses or bacteria and alcohol. A number of intracellular molecules have been identified that can stimulate other cells to produce proinflammatory cytokines and chemokines. Such proinflammatory cellular molecules are thought to function by engaging receptors on cytokine-producing cells. If left untreated, sterile inflammation may progress to non-alcoholic fatty liver disease (NAFLD), non-alcoholic steatohepatitis (NASH) or cyrrhosis.

"Non-alcoholic steatohepatitis" or "NASH" is a condition of the liver in which inflammation is caused by a buildup of fat in the liver. NASH is part of a group of liver diseases, known as nonalcoholic fatty liver disease, in which fat builds up in the liver and sometimes causes liver damage that gets worse over time (progressive liver damage). "Non-alcoholic fatty liver disease" (NAFLD) is fatty inflammation of the liver which is not due to excessive alcohol use. It is related to insulin resistance and the metabolic syndrome, obesity, high cholesterol and triglycerides, and diabetes, and may respond to treatments originally developed for other insulin resistant states (e.g. diabetes mellitus type 2), such as weight loss, metformin and thiazolidinediones. Non-alcoholic steatohepatitis (NASH) is the most extreme form of NAFLD, which is regarded as a major cause of cirrhosis of the liver of unknown cause.

Other factors that have been known to contribute to NASH include: surgery that shorten the intestines, the stomach, or both, such as jejunal bypass operation or biliopancreatic diversion; prolonged use of feeding tube or other method of receiving nutrition; certain drugs, including amiodarone, glucocorticoids, synthetic estrogens, and tamoxifen.

NASH is a condition that may get worse over time (called a progressive condition) and can cause scarring (fibrosis) of the liver, which leads to cirrhosis. "Cirrhosis" describes a condition in which liver cells have been replaced by scar tissue. The term "cirrhosis of the liver" or "cirrhosis" is used to describe a chronic liver disease characterized by replacement of liver tissue by fibrous scar tissue as well as regenerative nodules, leading to progressive loss of liver function. Cirrhosis is most commonly caused by fatty liver disease, including NASH, as well as alcoholism and hepatitis B and C, but also may be of unknown cause. Potentially life-threatening complications of cirrhosis are hepatic encephalopathy (confusion and coma) and bleeding from esophageal varices. Cirrhosis has historically been thought to be generally irreversible once it occurs, and historical treatment focused on preventing progression and complications. In advanced stages of cirrhosis, the only option is a liver transplant. Some embodiments of the present invention can be used to limit, inhibit, reduce the likelihood or treat cirrhosis of the liver without regard to its etiology.

Some embodiments of the present invention can be used to treat, prevent or control chemical liver trauma and hepatotoxicity. "Chemical trauma" or "acute chemical trauma" refers to serious injury which occurs to a patient over a short duration as a consequence of chemical toxicity, including drug-induced toxicity or trauma. Drug-induced acute liver trauma, including acetaminophen-induced acute liver trauma, is acute liver injury which occurs as a result or consequence of exposure to a drug (e.g., drug overdose), especially acetaminophen toxicity.

Hepatotoxocity is chemical liver trauma resulting from a hepatotoxic agent, or hepatotoxicity-inducing bioactive agent. The terms "hepatotoxic agent" and "a hepatotoxicity inducing bioactive agent" are used synonymously in context to describe compounds which often produce hepatotoxicity in patients administered such agents. Examples of hepatoxicity agents include, for example, anaesthetic agents, antiviral agents, anti-retroviral agents (nucleoside reverse transcriptase inhibitors and non-nucleoside reverse transcriptase inhibitors), especially anti-HIV agents, anticancer agents, organ transplant drugs (cyclosporin, tacrolimus, OKT3), antimicrobial agents (anti-TB, anti-fungal, antibiotics), anti-diabetes drugs, vitamin A derivatives, steroidal agents, especially including oral contraceptives, anabolic steroids, androgens, non-steroidal anti-inflammatory agents, anti-depressants (especially tricyclic antidepressants) glucocorticoids, natural products and herbal and alternative remedies, especially including St. John's wort.

Hepatotoxicity may manifest as triglyceride accumulation which leads to either small droplet (microvesicular) or large droplet (macrovesicular) fatty liver. There is a separate type of steatosis where phospholipid accumulation leads to a pattern similar to the diseases with inherited phospholipid metabolism defects (e.g., Tay-Sachs disease).

Some embodiments of the present invention can be used to treat, prevent or control chronic liver disease. Chronic liver disease is marked by the gradual destruction of liver tissue over time. Several liver diseases fall under this category, including cirrhosis and fibrosis, the latter of which is often the precursor to cirrhosis. Cirrhosis is the result of acute and chronic liver disease and is characterized by the replacement of liver tissue by fibrotic scar tissue and regenerative nodules leading to a progressive loss of liver function. Fibrosis and nodular regeneration results in the loss of the normal microscopic lobular architecture of the liver. Fibrosis represents the growth of scar tissue resulting from, for example, infection, inflammation, injury, and even healing. Over time, the fibrotic scar tissue slowly replaces the normal functioning liver tissue resulting in a decreasing amount of blood flow to the liver leaving the liver incapable of fully processing nutrients, hormones, drugs, and poisons that are found in the bloodstream. More common causes of cirrhosis include alcoholism, hepatitis C viral infections, ingestion of toxins, and fatty liver, but many other possible causes also exist. Chronic hepatitis C virus (HCV) infection and non-alcoholic steatohepatitis (NASH) are the two major causes of chronic liver disease in the United States estimated to affect between 3-5 million people. A rising concern is the continuously increasing number of U.S. citizens, currently numbering over 30 million, with obesity and metabolic syndrome that have non-alcoholic fatty liver disease (NAFLD) with approximately 10% who will eventually develop NASH. Other bodily complications are a consequence of a loss of liver function. The most common complication of cirrhosis is a condition known as ascites, an accumulation of fluid in the peritoneal cavity, which can lead to an increased risk of spontaneous bacterial peritonitis possibly resulting in the premature death of the patient.

For example, the prediction of the glycemic response to food according to some embodiments of the present invention can be used for constructing a personalized diet to the subject under analysis. Such a diet can include for example, list of foods which maintain relatively low blood glucose levels, so as to prevent, reduce the risk of developing, control, and/or treat one or more of the above syndromes or diseases.

The method present embodiments can also be used to personally tailor a weight reducing or weight maintaining diet for healthy individuals in the general populations, from one of the existing diets in the market or through design of a new diet. Using the databases of the present embodiments the method of the present embodiments can optionally and preferably predict that healthy or disease-prone individuals may be placed on one of our state-of-the-art individual clusters, allowing to accurately predict their response to foods that were not consumed during the study period. In some embodiments, the method can be used to place people in clusters even based only on a portion of the data.

Following is a more detailed description of the method according to some embodiments of the present invention.

The present embodiments contemplate subject-specific and group databases that include additional data, aside from the foods and respective responses. In some embodiments at least one of the databases comprises one or more (e.g., a plurality of) multidimensional entries, each entry having at least three dimensions, in some embodiments at least one of the databases comprises one or more (e.g., a plurality of) multidimensional entries, each entry having at least four dimensions, in some embodiments at least one of the databases comprises one or more (e.g., a plurality of) multidimensional entries, each entry having at least five dimensions, and in some embodiments at least one of the databases comprises one or more (e.g., a plurality of) multidimensional entries, each entry having more than five dimensions.

The additional dimensions of the databases provides additional information pertaining to the subject under analysis, to the other subjects and/or to the foods consumed by the respective subjects. In the following, "an individual" collectively refers to a subject which can be the subject under analysis or another subject from the group database.

In some embodiments of the present invention the additional information pertains to a microbiome profile or a partial microbiome profile of the individual.

Typically, the microbiome of an individual is determined from a stool sample of the individual.

As used herein, the term "microbiome" refers to the totality of microbes (bacteria, fungae, protists), their genetic elements (genomes) in a defined environment.

The present embodiments encompass the recognition that microbial signatures can be relied upon as proxy for microbiome composition and/or activity. Microbial signatures comprise data points that are indicators of microbiome composition and/or activity. Thus, according to the present invention, changes in microbiomes can be detected and/or analyzed through detection of one or more features of microbial signatures.

In embodiments, a microbial signature includes information relating to absolute amount of one or more types of microbes, and/or products thereof. In some embodiments, a microbial signature includes information relating to relative amounts of five, ten, twenty or more types of microbes and/or products thereof.

In some embodiments, a microbial signature includes information relating to presence, level, and/or activity of at least ten types of microbes. In some embodiments, a microbial signature includes information relating to presence, level, and/or activity of between 5 and 100 types of microbes. In some embodiments, a microbial signature includes information relating to presence, level, and/or activity of between 100 and 1000 or more types of microbes. In some embodiments, a microbial signature includes information relating to presence, level, and/or activity of substantially all types of microbes within the microbiome.

In some embodiments, a microbial signature comprises a level or set of levels of at least five, or at least ten or more types of microbes or components or products thereof. In some embodiments, a microbial signature comprises a level or set of levels of at least five or at least ten or more DNA sequences. In some embodiments, a microbial signature comprises a level or set of levels of ten or more 16S rRNA gene sequences. In some embodiments, a microbial signature comprises a level or set of levels of 18S rRNA gene sequences. In some embodiments, a microbial signature comprises a level or set of levels of at least five or at least ten or more RNA transcripts. In some embodiments, a microbial signature comprises a level or set of levels of at least five or at least ten or more proteins. In some embodiments, a microbial signature comprises a level or set of levels of at least five or at least ten or more metabolites.

16S and 18S rRNA gene sequences encode small subunit components of prokaryotic and eukaryotic ribosomes respectively. rRNA genes are particularly useful in distinguishing between types of microbes because, although sequences of these genes differ between microbial species, the genes have highly conserved regions for primer binding. This specificity between conserved primer binding regions allows the rRNA genes of many different types of microbes to be amplified with a single set of primers and then to be distinguished by amplified sequences.

Preferably, the microbiome profile of the subject under analysis is included in the subject specific database, and the microbiome profiles of one or more (more preferably all) of the other subjects is included in the group database. When the subject specific database includes the microbiome profile, the microbiome profile can be included as a separate entry. When the group database includes the microbiome profile, the microbiome profile is optionally and preferably included per subject. Thus, for example, a group database entry can be described by the tuple (S, F, R, {M}), where S, F, and R have been introduced before and {M} is the microbiome profile of subject S.

The microbiome profile {M} optionally and preferably includes a plurality of values with each value representing the abundance of a particular microbe. The abundance of a particular microbe may be determined, for instance, by sequencing the nucleic acids of the microbiome. This sequencing data may then be analyzed by known software to determine the abundance of particular microbes of the individual.

It was found by the present inventors that obese individuals have a microbiome which is less diverse than that of lean people. Thus, analysis of databases that include microbiome profile is advantageous since it provides additional information regarding the similarities between the subject under analysis and the other subject, thereby increasing the accuracy of the predictability. It was also found by the present inventors that the microbiome profile relates to the blood glucose levels, through an association between insulin resistance and gut microbiota. Insulin resistance is a state in which the cells of the body do not respond to insulin produced by the pancreas. As a result, the body cannot lower the level of glucose in the blood. For example, there is a known an association between type 2 diabetes and the microbiome profile [Qin et al., 2012, Nature, 490(7418):55-60].

In some embodiments of the present invention the additional information pertains to an at least a partial blood chemistry of individual.

As used herein "blood chemistry" refers to the concentration, or concentrations, of any and all substances dissolved in, or comprising, the blood. Representative examples of such substances, include, without limitation, albumin, amylase, alkaline phosphatase, bicarbonate, total bilirubin, BUN, C-reactive protein, calcium, chloride, LDL, HDL, total cholesterol, creatinine, CPK, γ-GT, glucose, LDH, inorganic phosphorus, lipase, potassium, total protein, AST, ALT, sodium, triglycerides, uric acid and VLDL.

Preferably, the blood chemistry of the subject under analysis is included in the subject specific database, and the blood chemistry of one or more (more preferably all) of the other subjects is included in the group database. When the subject specific database includes the blood chemistry, the blood chemistry can be included as a separate entry. When the group database includes the blood chemistry, the blood chemistry is optionally and preferably included per subject. Thus, for example, a group database entry can be described by the tuple (S, F, R, {C}), where S, F, and R have been introduced before and {C} is the blood chemistry of subject S.

It was found by the present inventors that analysis of databases that include blood chemistry is advantageous since it provides additional information regarding the similarities between the subject under analysis and the other subject, thereby increasing the accuracy of the predictability.

In some embodiments of the present invention the additional information pertains to a genetic profile of individual.

As used herein "genetic profile" refers to the analysis of a number of different genes. A genetic profile can encompass the genes in an entire genome of the individual, or it can encompass a specific subset of genes. The genetic profile may include genomic profile, a proteomic profile, an epigenomic profile and/or a transcriptomic profile.

Preferably, the genetic profile of the subject under analysis is included in the subject specific database, and the genetic profile of one or more (more preferably all) of the other subjects is included in the group database. When the subject specific database includes the genetic profile, the genetic profile can be included as a separate entry. When the group database includes the genetic profile, the genetic profile is optionally and preferably included per subject. Thus, for example, a group database entry can be described by the tuple (S, F, R, {G}), where S, F, and R have been introduced before and {G} is the genetic profile of subject S.

It was found by the present inventors that analysis of databases that include genetic profile is advantageous since it provides additional information regarding the similarities between the subject under analysis and the other subject, thereby increasing the accuracy of the predictability.

In some embodiments of the present invention the additional information pertains to metabolomic data associated with the individual.

As used herein, the term "metabolome" refers to the collection of metabolites present in the individual. The human metabolome encompasses native small molecules (natively biosynthesizeable, non-polymeric compounds) that are participants in general metabolic reactions and that are required for the maintenance, growth and normal function of a cell. Typically, metabolites are small molecule compounds, such as substrates for enzymes of metabolic pathways, intermediates of such pathways or the products obtained by a metabolic pathway.

Representative examples of metabolic pathways that are contemplated according to some embodiments of the present invention include, without limitation, at least citric acid cycle, respiratory chain, photosynthesis, photorespiration, glycolysis, gluconeogenesis, hexose monophosphate pathway, oxidative pentose phosphate pathway, production and (3-oxidation of fatty acids, urea cycle, amino acid biosynthesis pathways, protein degradation pathways such as proteasomal degradation, amino acid degrading pathways, biosynthesis or degradation of: lipids, polyketides (including, e.g., flavonoids and isoflavonoids), isoprenoids (including, e.g., terpenes, sterols, steroids, carotenoids, xanthophylls), carbohydrates, phenylpropanoids and derivatives, alkaloids, benzenoids, indoles, indole-sulfur compounds, porphyrins, anthocyans, hormones, vitamins, cofactors such as prosthetic groups or electron carriers, lignin, glucosinolates, purines, pyrimidines, nucleosides, nucleotides and related molecules such as tRNAs, microRNAs (miRNA) or mRNAs.

Thus, the metabolome is a direct observation of the status of cellular physiology, and can therefore be used for defining similarities between the subject under analysis and the other subject. The metabolomic data can be the metabolome or a portion thereof, namely, data that include some but not all the metabolites present in the individual.

Preferably, the metabolomic data of the subject under analysis is included in the subject specific database, and the metabolomic data of one or more (more preferably all) of the other subjects is included in the group database. When the subject specific database includes the metabolomic data, the metabolomic data can be included as a separate entry. When the group database includes the metabolomic data, the metabolomic data is optionally and preferably included per subject. Thus, for example, a group database entry can be described by the tuple (S, F, R, {B}), where S, F, and R have been introduced before and {B} is the metabolomic data of subject S.

In some embodiments of the present invention the additional information pertains to the medical condition of the individual. The medical condition optionally and preferably includes a list of diseases or syndromes (if present) the subject is experiencing or has experienced in the past. The medical condition can be obtained, for example, by means of a questionnaire presented to the respective individual during the construction or update of the database.

Preferably, the medical condition of the subject under analysis is included in the subject specific database, and the medical condition of one or more (more preferably all) of the other subjects is included in the group database. When the subject specific database includes the medical condition, the medical condition can be included as a separate entry. When the group database includes the medical condition, the medical condition is optionally and preferably included per subject. Thus, for example, a group database entry can be described by the tuple (S, F, R, {D}), where S, F, and R have been introduced before and {D} is the medical condition of subject S.

In some embodiments of the present invention the additional information pertains to food intake habits of the individual. The food intake habits can include a list of foods which are regularly consumed by the individual, optionally together with corresponding intake frequencies. The intake frequency represents the estimated number of times or volume or weight of the food that the individual has a habit of consuming over a time period (e.g., 24 hours, week, etc.). The food intake habits can also be obtained by means of a questionnaire. Since the food intake habits are obtained by a questionnaire, the lists of foods in the food intake habits may optionally comprise foods for which the response of the individual is not known.

Preferably, the food intake habits of the subject under analysis is included in the subject specific database, and the food intake habits of one or more (more preferably all) of the other subjects is included in the group database. When the subject specific database includes the food intake habits, the food intake habits can be included as a separate entry. When the group database includes the food intake habits, the food intake habits are optionally and preferably included per subject. Thus, for example, a group database entry can be described by the tuple (S, F, R, {I}), where S, F, and R have been introduced before and {I} is the food intake habits of subject S.

In some embodiments of the present invention the additional information pertains to activities performed by individual over a time period. This information can be provided as a listing of discrete activities (sleeping, exercising, sitting, resting, etc.) performed by the individual over the time period. The activities are optionally and preferably provided in relation to foods consumed during the activities and/or response to food (e.g., blood sucrose levels) measured during the activities.

Preferably, the listing of discrete activities of the subject under analysis is included in the subject specific database, and the listing of discrete activities of one or more (more preferably all) of the other subjects is included in the group database. The activities are optionally and preferably included per response entry in the database. Thus, for example, a group database entry can be described by the tuple (S, F, R, {A}), where S, F, and R have been introduced before and {A} is an activity performed by subject S during response R. Similarly, a subject-specific database entry can be described by the tuple (F, R, {A}). The databases can also include entries which include an activity performed by the individual which is not associated with a particular food. This is because for some measured glucose levels it is unknown whether these levels are a response of the individual to a particular food. Thus, some group database entries can also be described by the tuple (S, R, {A}), and some subject-specific database entries can be described by the tuple (R, {A}).

In some embodiments of the present invention the additional information pertains to a characteristic intake frequency associated with a respective food consumed by the respective individual. Unlike the food intake habits defined above, the characteristic intake frequency is provided for foods to which the response of the individual is known, and is therefore optionally and preferably provided per food entry in the databases. Thus, one or more of the entries of the subject-specific database can be represented as a tuple (F, R, f), one or more of the entries of the group database can be represented as a tuple (S, F, R, f), where S, F and R have been introduced above, and f is the intake frequency associated with food F. The intake frequency represents the number of times or the volume or weight of the food that is consumed by the individual over a time period (e.g., 24 hours, week, etc.).

In some embodiments of the present invention the additional information pertains to an at least a partial chemical composition of the food. In these embodiments, one or more of the entries of the subject-specific database can be represented as a tuple (F, R, {L}), and one or more of the entries of the group database can be represented as a tuple (S, F, R, {L}), where S, F and R have been introduced above, and {L} is the chemical composition or partial chemical composition of food F.

It is to be understood that while the above types of additional information were described separately, the present embodiments contemplate any combination of two or more types of information for the databases. For example, one or more of the entries of the group database can be represented as a tuple (S, F, R, {X}), where {X} represents a data structure that includes two or more of: the microbiome profile, the blood chemistry, the genetic profile, the metabolomic data, the medical condition, the food intake habits, the activities and the chemical composition as described above.

Similarly, two or more of the above information types can be included either as separate entries or as additional dimensions supplemented to the tuple (F, R) of the subject-specific database.

The analysis of the subject-specific and group databases based on the selected food optionally and preferably comprises a traversal over the databases or some selected parts thereof and a search for similarities between data objects in the subject-specific database and data objects in the group database. The similarities are then used to define a portion of the group database which is narrower than the database or part thereof that was searched. The response to the selected food can then be extracted from the narrowed portion of the group database.

If several responses to the selected food are found in the group database, a likelihood test may optionally and preferably be executed so as to extract a response having higher likelihood to be a response of the subject under analysis. Alternatively, an averaging procedure can be applied to the found responses. Still alternatively, the search for similarities can be repeated so as to define a portion of the group database which is narrower than the previously defined portion. This process can be iteratively repeated until a response of other subjects to the selected food can be extracted.

The present embodiments also contemplate an analysis procedure for a situation in which no response to the selected food is found in the group database. In this situation, the group database optionally and preferably includes responses of one or more other subjects to a food which is similar to the selected food, and the method can select from the group database one or more foods that are similar to the selected food. The method can then perform one or more of the above procedures as if those foods were selected at 11.

The similarity between foods can be based, for example, on food groups, wherein two foods that contain similar relative amounts of the same food group can be considered similar. Thus, in these embodiments, the group database comprises responses of one or more other subjects to a food containing one or more (e.g., 2, 3, 4, 5 or more) food groups that are also contained in the selected group, optionally and preferably at the same, or approximately the same (e.g., within 10%), relative amounts. For example, when the selected food contains a certain relative amount P of food group G, and the group database does not contain the selected food, the method can select from the group database one or more foods for which the amounts of food group G are similar (e.g., within 10%) to P, and perform one or more of the above procedures as if those foods were selected at 11. The food group G can be any of the aforementioned food groups (e.g., carbohydrates, proteins, fats, minerals, vitamins etc.). It is appreciate that more than one food group can be used for determining the similarity. For example, when the selected food contains relative amounts $P_1, P_2, \ldots, P_N$ of respective food groups $G_1, G_2, \ldots, G_N$, and the group database does not contain the selected food, the method can select from the group database one or more foods for which the amounts of food group $G_1$ are similar (e.g., within 10%) to $P_1$, the amounts of food group $G_2$ are similar (e.g., within 10%) to $P_2$, etc.

In some embodiments of the present invention the group database comprises data classified according to a predetermined set of classification groups. The classification can be based on any dimension of the data as described above. In these embodiments, the analysis comprises classifying the subject according to the same set of classification groups. The response of the subject to the selected food can then be estimated based on responses in the group database that correspond to the classification group to which the subject is classified.

The analysis of the databases according to some embodiments of the present invention comprises executing a machine learning procedure.

As used herein the term "machine learning" refers to a procedure embodied as a computer program configured to induce patterns, regularities, or rules from previously collected data to develop an appropriate response to future data, or describe the data in some meaningful way.

Use of machine learning is particularly, but not exclusively, advantageous when the database includes multidimensional entries.

The group and subject databases can be used as a training set from which the machine learning procedure can extract parameters that best describe the dataset. Once the parameters are extracted, they can be used to predict the response for the selected food.

In machine learning, information can be acquired via supervised learning or unsupervised learning. In some embodiments of the invention the machine learning procedure comprises, or is, a supervised learning procedure. In supervised learning, global or local goal functions are used to optimize the structure of the learning system. In other words, in supervised learning there is a desired response, which is used by the system to guide the learning.

In some embodiments of the invention the machine learning procedure comprises, or is, an unsupervised learning procedure. In unsupervised learning there are typically no goal functions. In particular, the learning system is not provided with a set of rules. One form of unsupervised, learning according to some embodiments of the present invention, is unsupervised clustering in which the data objects are not class labeled, a priori.

Representative examples of "machine learning" procedures suitable for the present embodiments, including, without limitation, clustering, association rule algorithms, feature evaluation algorithms, subset selection algorithms, support vector machines, classification rules, cost-sensitive classifiers, vote algorithms, stacking algorithms, Bayesian networks, decision trees, neural networks, instance-based algorithms, linear modeling algorithms, k-nearest neighbors analysis, ensemble learning algorithms, probabilistic models, graphical models, regression methods, gradient ascent methods, singular value decomposition methods and principle component analysis. Among neural network models, the self-organizing map and adaptive resonance theory are commonly used unsupervised learning algorithms. The adaptive resonance theory model allows the number of clusters to vary with problem size and lets the user control the degree of similarity between members of the same clusters by means of a user-defined constant called the vigilance parameter.

Following is an overview of some machine learning procedures suitable for the present embodiments.

Association rule algorithm is a technique for extracting meaningful association patterns among features.

The term "association", in the context of machine learning, refers to any interrelation among features, not just ones that predict a particular class or numeric value. Association includes, but it is not limited to, finding association rules, finding patterns, performing feature evaluation, performing feature subset selection, developing predictive models, and understanding interactions between features.

The term "association rules" refers to elements that co-occur frequently within the databases. It includes, but is not limited to association patterns, discriminative patterns, frequent patterns, closed patterns, and colossal patterns.

A usual primary step of association rule algorithm is to find a set of items or features that are most frequent among all the observations. Once the list is obtained, rules can be extracted from them.

The aforementioned self-organizing map is an unsupervised learning technique often used for visualization and analysis of high-dimensional data. Typical applications are focused on the visualization of the central dependencies within the data on the map. The map generated by the algorithm can be used to speed up the identification of association rules by other algorithms. The algorithm typically includes a grid of processing units, referred to as "neurons". Each neuron is associated with a feature vector referred to as observation. The map attempts to represent all the available observations with optimal accuracy using a restricted set of models. At the same time the models become ordered on the grid so that similar models are close to each other and dissimilar models far from each other. This procedure enables the identification as well as the visualization of dependencies or associations between the features in the data.

Feature evaluation algorithms are directed to the ranking of features or to the ranking followed by the selection of features based on their impact on the response of the subject under analysis to the selected food.

The term "feature" in the context of machine learning refers to one or more raw input variables, to one or more processed variables, or to one or more mathematical combinations of other variables, including raw variables and processed variables. Features may be continuous or discrete.

Information gain is one of the machine learning methods suitable for feature evaluation. The definition of information gain requires the definition of entropy, which is a measure of impurity in a collection of training instances. The reduction in entropy of the target feature that occurs by knowing the values of a certain feature is called information gain. Information gain may be used as a parameter to determine the effectiveness of a feature in explaining the response of the subject under analysis to the selected food. Symmetrical uncertainty is an algorithm that can be used by a feature selection algorithm, according to some embodiments of the present invention. Symmetrical uncertainty compensates for information gain's bias towards features with more values by normalizing features to a [0,1] range.

Subset selection algorithms rely on a combination of an evaluation algorithm and a search algorithm. Similarly to feature evaluation algorithms, subset selection algorithms rank subsets of features. Unlike feature evaluation algorithms, however, a subset selection algorithm suitable for the present embodiments aims at selecting the subset of features with the highest impact on the response of the subject under analysis to the selected food, while accounting for the degree of redundancy between the features included in the subset. The benefits from feature subset selection include facilitating data visualization and understanding, reducing measurement and storage requirements, reducing training and utilization times, and eliminating distracting features to improve classification.

Two basic approaches to subset selection algorithms are the process of adding features to a working subset (forward selection) and deleting from the current subset of features (backward elimination). In machine learning, forward selection is done differently than the statistical procedure with the same name. The feature to be added to the current subset in machine learning is found by evaluating the performance of the current subset augmented by one new feature using cross-validation. In forward selection, subsets are built up by adding each remaining feature in turn to the current subset while evaluating the expected performance of each new subset using cross-validation. The feature that leads to the best performance when added to the current subset is retained and the process continues. The search ends when none of the remaining available features improves the predictive ability of the current subset. This process finds a local optimum set of features.

Backward elimination is implemented in a similar fashion. With backward elimination, the search ends when further reduction in the feature set does not improve the predictive ability of the subset. The present embodiments contemplate search algorithms that search forward, backward or in both directions. Representative examples of search algorithms suitable for the present embodiments include, without limitation, exhaustive search, greedy hill-climbing, random perturbations of subsets, wrapper algorithms, probabilistic race search, schemata search, rank race search, and Bayesian classifier.

A decision tree is a decision support algorithm that forms a logical pathway of steps involved in considering the input to make a decision.

The term "decision tree" refers to any type of tree-based learning algorithms, including, but not limited to, model trees, classification trees, and regression trees.

A decision tree can be used to classify the databases or their relation hierarchically. The decision tree has tree structure that includes branch nodes and leaf nodes. Each branch node specifies an attribute (splitting attribute) and a test (splitting test) to be carried out on the value of the splitting attribute, and branches out to other nodes for all possible outcomes of the splitting test. The branch node that is the root of the decision tree is called the root node. Each leaf node can represent a classification (e.g., whether a particular portion of the group database matches a particular portion of the subject-specific database) or a value (e.g., a predicted response of the subject under analysis to the selected food). The leaf nodes can also contain additional information about the represented classification such as a confidence score that measures a confidence in the represented classification (i.e., the likelihood of the classification being accurate). For example, the confidence score can be a continuous value ranging from 0 to 1, which a score of 0 indicating a very low confidence (e.g., the indication value of the represented classification is very low) and a score of 1 indicating a very high confidence (e.g., the represented classification is almost certainly accurate). The response of the subject to the selected food can be classified by traversing down the decision tree based on outcomes of the splitting tests of the branch nodes on the path until a leaf node is reached, which provides the response of the subject to the selected food.

Support vector machines are algorithms that are based on statistical learning theory. A support vector machine (SVM) according to some embodiments of the present invention can be used for classification purposes and/or for numeric prediction. A support vector machine for classification is referred to herein as "support vector classifier," support vector machine for numeric prediction is referred to herein as "support vector regression".

An SVM is typically characterized by a kernel function, the selection of which determines whether the resulting SVM provides classification, regression or other functions. Through application of the kernel function, the SVM maps input vectors into high dimensional feature space, in which a decision hyper-surface (also known as a separator) can be constructed to provide classification, regression or other decision functions. In the simplest case, the surface is a hyper-plane (also known as linear separator), but more complex separators are also contemplated and can be applied using kernel functions. The data points that define the hyper-surface are referred to as support vectors.

The support vector classifier selects a separator where the distance of the separator from the closest data points is as large as possible, thereby separating feature vector points associated with objects in a given class from feature vector points associated with objects outside the class. For support vector regression, a high-dimensional tube with a radius of acceptable error is constructed which minimizes the error of the data set while also maximizing the flatness of the associated curve or function. In other words, the tube is an envelope around the fit curve, defined by a collection of data points nearest the curve or surface.

An advantage of a support vector machine is that once the support vectors have been identified, the remaining observations can be removed from the calculations, thus greatly reducing the computational complexity of the problem. An SVM typically operates in two phases: a training phase and a testing phase. During the training phase, a set of support vectors is generated for use in executing the decision rule. During the testing phase, decisions are made using the decision rule. A support vector algorithm is a method for training an SVM. By execution of the algorithm, a training set of parameters is generated, including the support vectors that characterize the SVM. A representative example of a support vector algorithm suitable for the present embodiments includes, without limitation, sequential minimal optimization.

The Least Absolute Shrinkage and Selection Operator (LASSO) algorithm is a shrinkage and/or selection algorithm for linear regression. The LASSO algorithm may minimizes the usual sum of squared errors, with a regularization, that can be an L1 norm regularization (a bound on the sum of the absolute values of the coefficients), an L2 norm regularization (a bound on the sum of squares of the coefficients), and the like. The LASSO algorithm may be associated with soft-thresholding of wavelet coefficients, forward stagewise regression, and boosting methods. The LASSO algorithm is described in the paper: Tibshirani, R, Regression Shrinkage and Selection via the Lasso, J. Royal. Statist. Soc B., Vol. 58, No. 1, 1996, pages 267-288, the disclosure of which is incorporated herein by reference.

A Bayesian network is a model that represents variables and conditional interdependencies between variables. In a Bayesian network variables are represented as nodes, and nodes may be connected to one another by one or more links. A link indicates a relationship between two nodes. Nodes typically have corresponding conditional probability tables that are used to determine the probability of a state of a node given the state of other nodes to which the node is connected. In some embodiments, a Bayes optimal classifier algorithm is employed to apply the maximum a posteriori hypothesis to a new record in order to predict the probability of its classification, as well as to calculate the probabilities from each of the other hypotheses obtained from a training set and to use these probabilities as weighting factors for future predictions of the response to food. An algorithm suitable for a search for the best Bayesian network, includes, without limitation, global score metric-based algorithm. In an alternative approach to building the network, Markov blanket can be employed. The Markov blanket isolates a node from being affected by any node outside its boundary, which is composed of the node's parents, its children, and the parents of its children.

Instance-based algorithms generate a new model for each instance, instead of basing predictions on trees or networks generated (once) from a training set.

The term "instance", in the context of machine learning, refers to an example from a database.

Instance-based algorithms typically store the entire database in memory and build a model from a set of records similar to those being tested. This similarity can be evaluated, for example, through nearest-neighbor or locally weighted methods, e.g., using Euclidian distances. Once a set of records is selected, the final model may be built using several different algorithms, such as the naive Bayes.

Figure 3:
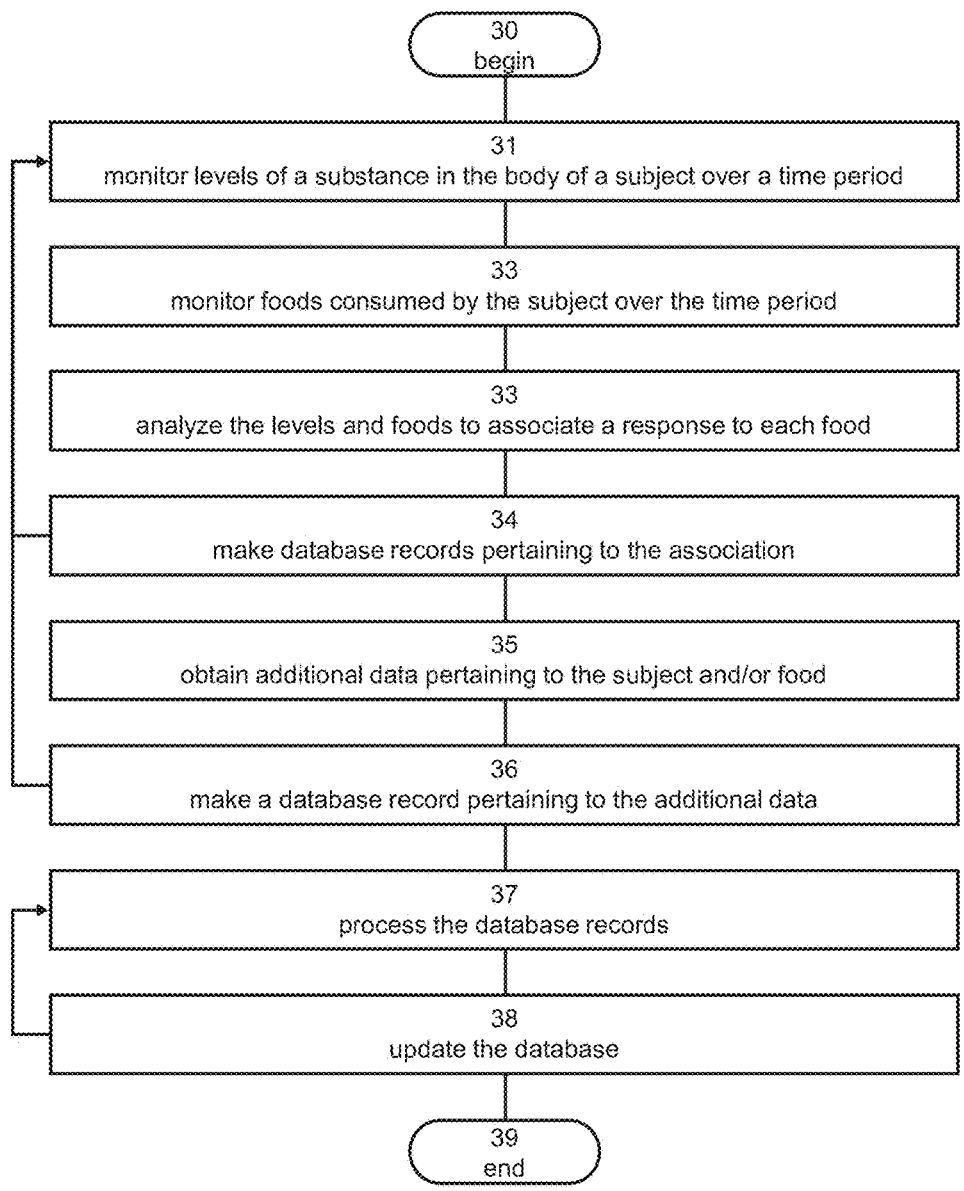

Reference is now made to FIG. 3 which is a flowchart diagram of a method suitable for constructing a database, according to some embodiments of the present invention.

The database can be constructed from data collected from a single subject or a group of subjects. When the data are collected from a single subject the constructed data database can be used as a subject-specific database (e.g., database 22) for method 10 above. When the data are collected from a group of subjects the constructed data database can be used as a group database (e.g., database 24) for method 10 above.

The method begins at 30 and continues to 31 at which levels of at least one substance in the body of a subject are monitored over a time period of at least a few days (e.g., a week). The substance can be one or more of glucose, cholesterol, sodium, potassium, calcium. In some embodiments of the invention the substance includes at least glucose, and in some exemplary embodiments of the invention the substance is glucose. The monitoring is can be continues or at a plurality of time instances (e.g., every 10 minutes or every 5 minutes or every 2 minutes or every 1 minute or every 30 seconds). Preferably, the levels are blood levels, e.g., blood glucose levels. The monitoring can be performed by a measuring device that is connected to the subject (e.g., to communicate with the vasculature of the subject) throughout the monitoring period.

The method continues to 32 at which foods consumed by the subject over a time period are monitored. The time period over which the consumed foods are monitored is optionally and preferably the same as the levels are monitored.

The method continues to 33 at which analyzing monitored levels and monitored foods to associate a response, e.g., glycemic response to each food of at least a portion of consumed foods. The analysis can be performed, for example, by plotting the consumed foods and levels on the same time axis and searching for patterns of level changes that are likely to occur responsively to food intake. To this end, a machine learning procedure, such as one or more of the above algorithms can be employed.

The method continues to 34 at which a database record pertaining to association is made in one or more databases, e.g., a group database or a subject specific database.

At 35 the method optionally and preferably obtains additional data pertaining to individual and/or food and making a record of additional data in at least one database. The additional data can describe any of the aforementioned types of additional information, including, without limitation, the microbiome profile, the blood chemistry, the genetic profile, the metabolomic data, the medical condition, the food intake habits, the activities and the chemical composition. The method optionally and preferably continues to 36 at which a database record pertaining to the additional data is made in one or more databases, e.g., a group database or a subject specific database. Preferably, 36 and 34 are applied to the same database. Thus, operation 36 results in a database having multidimensional entries as further detailed hereinabove. From 34 or 36 (if executed) the method can loops back to 31 and one or more of operations 31-36 can be performed for another subject. This loop is executed when it is desired to construct a group database.

In various exemplary embodiments of the invention the method continues to 37 at which the database records are processed, optionally and preferably using a multidimensional analysis procedure, and to 38 at which the database is updated responsively to the analysis. When the database is used as a subject-specific database, operation 37 preferably begins after data are collected for a single subject, and when the database is used as a group database, operation 37 preferably begins after data are collected for multiple subjects.

The multidimensional analysis procedure optionally and preferably comprises a machine learning procedure, such as one or more of the procedures described above. The purpose of the analysis is to determine patterns in the data that allow finding similarities among different entries in the database. For example, the analysis can include defining classification groups into which the database entries can be classified, and classifying the database entries according to the classification groups. Subsequently, entries can be labeled according to their classification. The multidimensional analysis can additionally or alternatively comprise the construction of a decision tree. Subsequently, the database can be updated to include the constructed decision tree. The multidimensional analysis can additionally or alternatively comprise extraction association patterns and/or association rules among features in the database. Subsequently, the database can be updated to include the association patterns and/or association rules. The multidimensional analysis can additionally or alternatively comprise ranking of features in the database, e.g., using feature evaluation algorithm. Subsequently, the database can be updated to include the ranks. The multidimensional analysis can additionally or alternatively comprise constructing a Bayesian network from at least a portion of the data of the database. Subsequently, the database can be updated to include the constructed Bayesian network. Other types of analyses are also contemplated.

The processing and updating of the database can be repeated one or more time. In these embodiments, the method can loop back from 38 to 37.

The method ends at 39.

As used herein the term "about" refers to ±10%.

The word "exemplary" is used herein to mean "serving as an example, instance or illustration." Any embodiment described as "exemplary" is not necessarily to be construed as preferred or advantageous over other embodiments and/or to exclude the incorporation of features from other embodiments.

The word "optionally" is used herein to mean "is provided in some embodiments and not provided in other embodiments." Any particular embodiment of the invention may include a plurality of "optional" features unless such features conflict.

The terms "comprises", "comprising", "includes", "including", "having" and their conjugates mean "including but not limited to".

The term "consisting of" means "including and limited to".

The term "consisting essentially of" means that the composition, method or structure may include additional ingredients, steps and/or parts, but only if the additional ingredients, steps and/or parts do not materially alter the basic and novel characteristics of the claimed composition, method or structure.

As used herein, the singular form "a", "an" and "the" include plural references unless the context clearly dictates otherwise. For example, the term "a compound" or "at least one compound" may include a plurality of compounds, including mixtures thereof.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Various embodiments and aspects of the present invention as delineated hereinabove and as claimed in the claims section below find experimental support in the following examples.

EXAMPLES

Reference is now made to the following examples, which together with the above descriptions illustrate some embodiments of the invention in a non limiting fashion.

Example 1

Blood glucose levels are rapidly elevating in the general population, resulting in a sharp incline in the prevalence of pre-diabetes and impaired glucose tolerance, and eventual development of type II diabetes mellitus. Dietary intake and food composition are considered central determinants of glucose levels and critically involved in glucose homeostasis in normoglycemic and pre-diabetic individuals alike. Indeed, dietary modifications in pre-diabetics can result in full reversal of hyperglycemia and its long-term complications. However, the individualized effects of food intake on the glycemic response remain poorly understood, thus substantially limiting the ability to effectively induce glycemic control through dietary intervention. This major obstacle stems from the substantial and poorly understood individual variability in the glycemic response to foods. A critical, yet poorly studied determinant of this diet-related variability is the composition and function of the intestinal microbiota.

The present Example presents a combined experimental and computational study which included a large-scale prospective analysis of the blood sugar response of normoglycemic and pre-diabetic individuals to food, and deciphering the microbiota contribution to this response. The microbiota and glycemic response of hundreds of individuals to food intake, and the different types of glycemic response patterns have been characterized. A personalized machine-learning algorithm for predicting the individualized glycemic response to food intake has been devised.

Methods 217 healthy volunteers were recruited at the Tel-Aviv Sourasky Medical Center. Of these, 182 completed the full study and for each of them, a multidimensional profile has been obtained and recorded in a group database. The profile included: (1) General lifestyle and health questionnaire; (2) Food frequency questionnaire (FFQ); (3) Extensive blood chemistry panel; (4) General physical parameters (e.g., body weight, height, waist size, blood pressure); (5) Comprehensive host genetic profile; (6) Full microbiome profiling (both composition by 16s rDNA profiling, and shotgun metogenomic sequencing; (7) One full week of blood glucose measurements using a continuous glucose monitor (CGM); (8) Comprehensive metabolomic profiling of samples; and (9) Log of one full week including times and content of food intake, physical activity, sleep times, and stress and hunger levels; (10) Glucose response to seven pre-defined test foods.

The database was analyzed by computer software, with the goal of characterizing the different types of glycemic response patterns that exist among subjects, and predicting the glycemic response of an individual to food intake.

Collecting a Comprehensive Metabolic, Genetic, and Microbiota Profile

Participants arrived at the Tel-Aviv Sourasky Medical Center. Each participant signed a consent form, and information/samples were obtained. All of the data and samples below were stored anonymously in databases and laboratories, respectively, under unique participant identifiers that do not allow identification of participants.

The following information and samples were obtained from each participant:

1) General lifestyle and health questionnaire filled out by each participant, including a comprehensive set of questions on past and existing medical conditions and lifestyle habits (e.g., exercise and smoking habits).

2) Food frequency questionnaire (FFQ), filled out by each participant, including a comprehensive set of questions on dietary habits and daily consumption of various food categories.

3) Extensive blood chemistry panel (e.g., cholesterol levels, complete blood counts, HbA1c), measured from blood drawn by us from each participant.

4) General physical parameters measured by us (e.g., body weight, height, waist size, blood pressure).

5) Comprehensive host genetic profile, obtained by Illumina arrays measuring about 700,000 different single nucleotide polymorphisms (SNP), applied to DNA extracted from blood drawn from participants upon their arrival to the center.

6) Comprehensive microbiota profiling, obtained by performing both 16S and metagenome analysis to DNA extracted from stool sample provided by each participant upon his/her arrival at our center.

Figure 4:
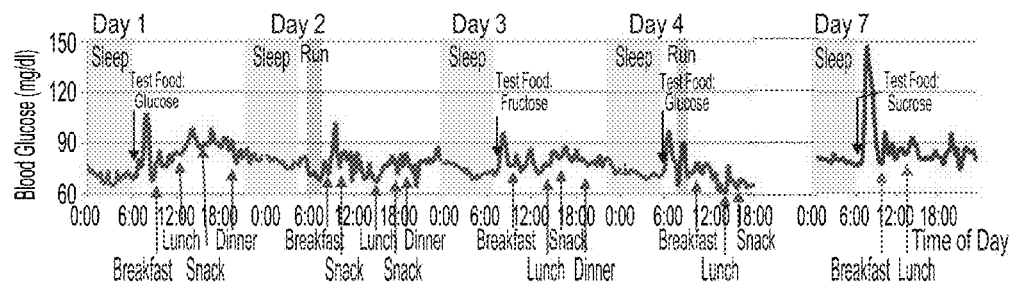

7) Continuous glucose measurements for one full week measured by connecting each participant for one full week to an iPro2 Continuous Glucose Monitor (CGM) which measures glucose levels every five minutes. An example of one measurement day for one participant is shown in FIG. 4. Shown in FIG. 4 is an example of raw blood glucose measurements of one participant in the study during seven connection days. Times of meal consumption are indicated with arrows; sleep time is also indicated.

8) Full metabolomic profiling of samples, performed by applying LC-MS and GC-MS mass spectrometry analyses to the collected stool and blood samples.

9) Activity log of one full week including all times and types of activities that each participant performed during the connection week and which could affect his/her blood glucose levels (e.g., content and times of all food intake, times and intensity of physical activity, sleeping times, and stress and hunger levels).

10) Glucose response to seven pre-defined test foods. Each morning, every participant consumed one of seven test meals provided by the staff which included precisely 50 g of available carbohydrates (plain white bread was consumed twice, plain white bread with 30 g of butter was consumed twice, 50 g of glucose was consumed twice with 250 g of water, and 50 g of fructose was consumed once with 250 g of water).

Results

Deviation Across Individuals in the Glucose Response to the Same Food

The extent to which different individuals exhibit different responses to the same food was examined. To this end, the blood glucose response of individuals were compared to the seven pre-defined test foods that they were each asked to consume in every morning of the study and which were supplied by the staff. Differences in the response of individuals to the same food for all types of test foods examined were found. Some individuals exhibited nearly no glycemic response to a food challenge of 50 g of available carbohydrates (even to pure glucose) while other individuals exhibited highly marked responses.

FIGS. 5A-F show histograms of the blood glucose response of participants in the study to Glucose (FIG. 5A), Bread (FIG. 5B) and Bread with butter (FIG. 5C), where the quantity of each food consumed was set such that the total carbohydrate content was 50 grams. Also shown are examples of the postprandial response of three individuals with a high glucose response and three individuals with a low glucose response to Glucose (FIG. 5D), Bread (FIG. 5E), and Bread with butter (FIG. 5F). Note that on average, butter reduces the glycemic response, although this is only the case for a subset of the individuals.

It was surprisingly found by the present inventors that the variability in response to food across different subjects is considerably high. The variability across different subjects is demonstrated in FIG. 5G which shows clustering of the response of different subjects to glucose, bread, and bread with butter. Each row in FIG. 5G corresponds to one subject, and colored entries represent the strength of the glycemic response to each food challenge (red indicates higher response and green indicates lower response). As shown, there are clusters of subjects with similar responses within each cluster, with about 10% of the subjects responding most strongly to bread with butter, about 30% to bread, and about 60% to pure glucose.

It was verified that the variation was not due to inaccuracy of the continuous glucose measurements, since (1) the average glucose response measured across the population closely matches the published glycemic responses of these foods which were also computed on population averages, and (2) a high degree of reproducibility within individuals in their response to the same food was found through comparison of the two replicate measurements that they were each asked to perform for three different types of pre-defined test foods. FIGS. 6A-C show comparison of the glucose response of two replicate measurements of Glucose (FIG. 6A), Bread (FIG. 6B) and Bread with butter (FIG. 6C), where the quantity of each food consumed was set such that the total carbohydrate content was 50 grams. Every point represents one study participant. The correlations across replicates are in the range 0.76-0.78 for the three different types of test foods.

Predictions of the Personal Response of Individuals to Food

To assess the ability to predict unseen meals, a cross validation scheme was employed. About 8,000 meals (for which glucose response measurements were obtained) were randomly partitioned into 10 equally sized sets. The glucose response of the meals in each set was predicted using a model whose parameters were learned using only the meals in the other 9 meal sets. Thus, every meal whose predictions are assessed was not observed during the model learning phase, thereby representing a true assessment of the predictive power of the present embodiments.

Three different models were compared, as follows:

1) One size fits all carbohydrate-only based model. This model used only one feature from each meal, namely the amount of carbohydrates contained in the meal, the rationale being that carbohydrates are a major known determinant of glycemic responses.

2) One size fits all multiple meal feature model. This model extends the carbohydrate-only model to include 10 additional parameters, consisting of: the meal weight, number of calories, protein amount, fat amount, carbohydrate fraction of meal, protein fraction of meal, fat fraction of meal, carbohydrates to protein log-ratio, carbohydrates to fat log-ratio, and the number of food components in the meal.

3) Personalized model. This model used the parameters of model 2, but in addition, also included:

a) Three personal clinical parameters, consisting of age, glycated haemoglobin levels in the blood (HbA1c), and phosphorous levels in the blood.

b) Four parameters from the previous meal (for meals consumed within the past 10 hours) consisting of the amount of calories, carbohydrates, carbohydrates to fat ratio of the previous meal as well as the time itself that passed since the previous meal.

Figure 7A:
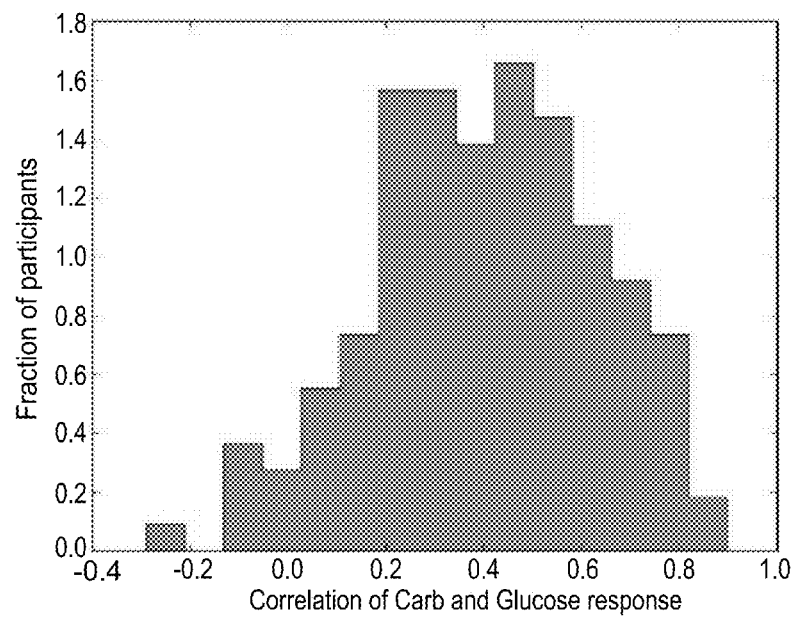
Figure 7B:
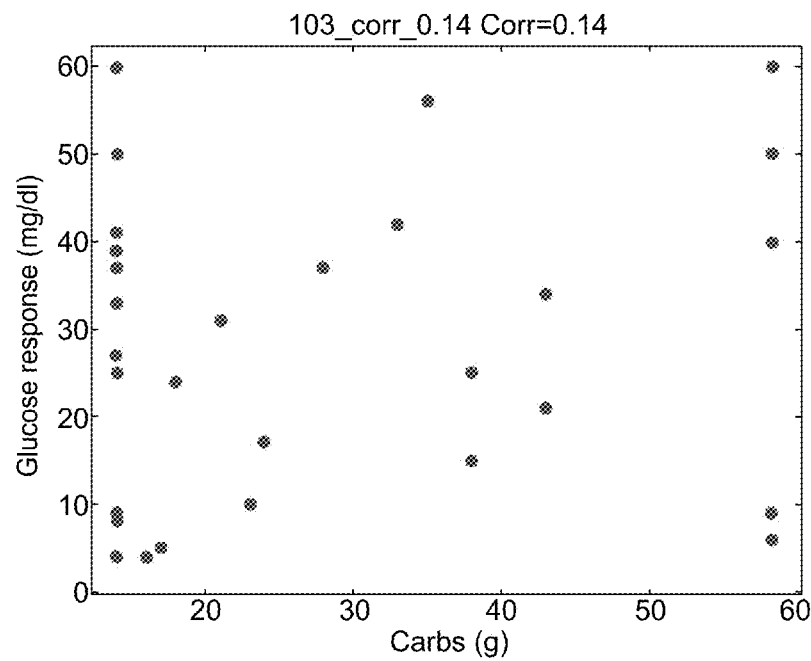
Figure 7C:
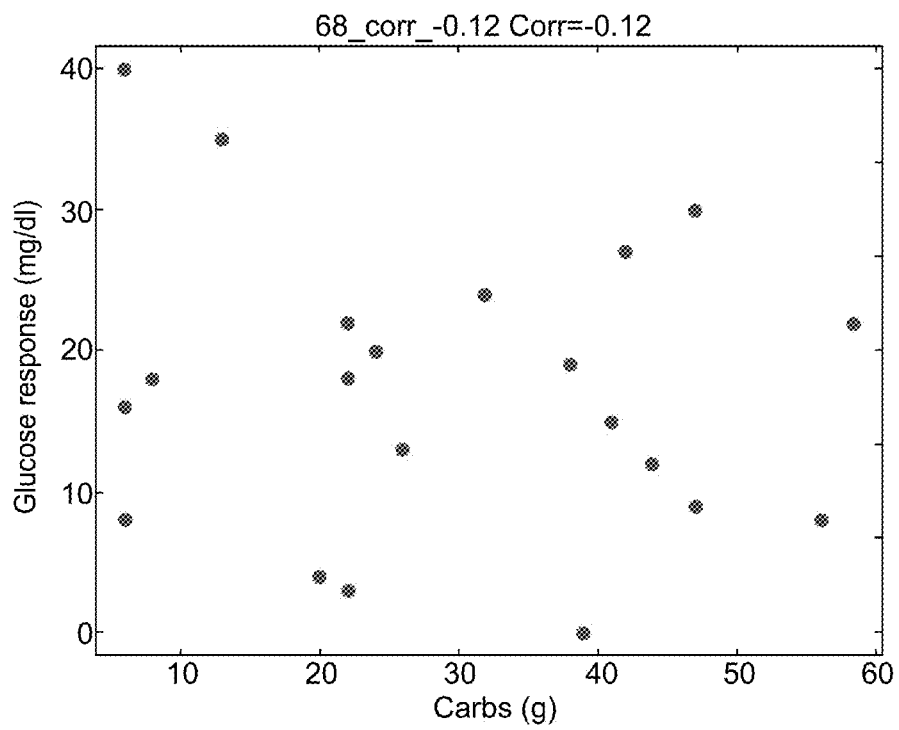
Figure 7D:
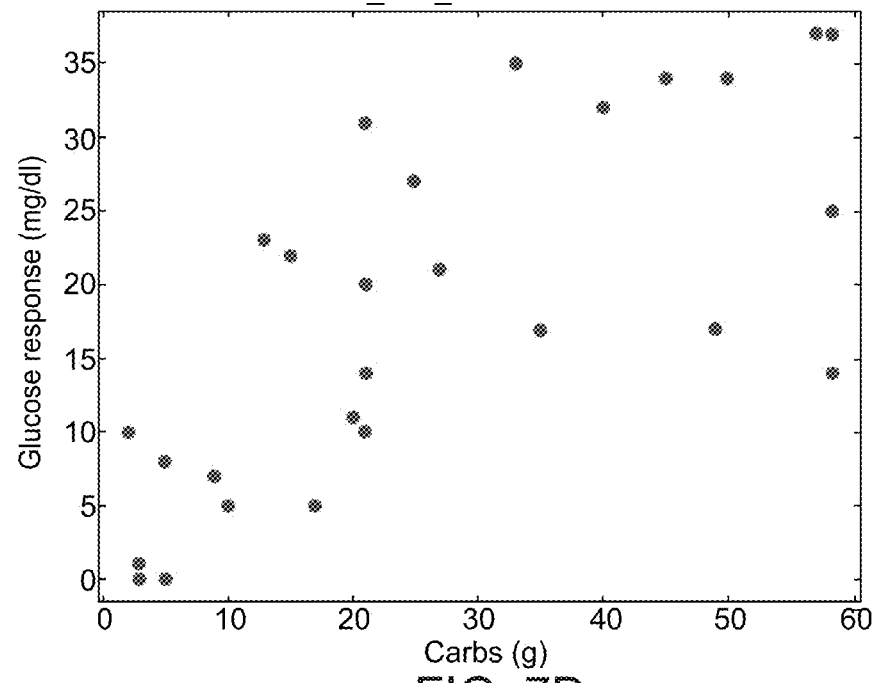
Figure 7E:
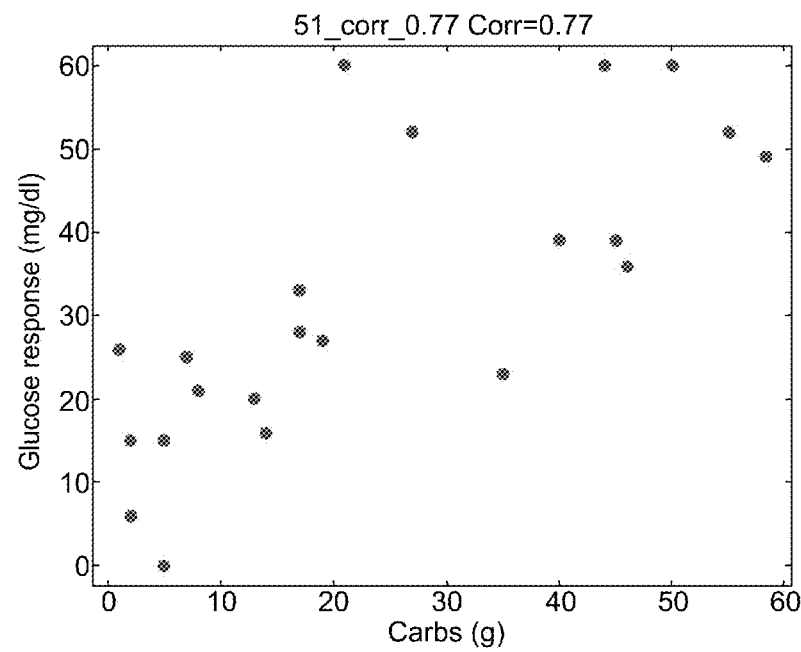

Individuals from the study were clustered into three distinct groups based only on the training data (i.e., the meals used to construct the predictor and not the held out meals that were predicted). A separate model was then constructed for each of the three different groups of people. The groups were defined based on the correlation that each person had between the amount of carbohydrates in the meal and his/her glucose response. The present inventors noticed that this relationship between the amount of carbohydrates and the glucose response varied greatly across individuals and thus sought to use this feature to construct separate predictors for each sub-population or cluster. FIGS. 7A-E demonstrate the rationale for this model, where the high degree of variability across people in the relationship between carbohydrate amount and the glucose response can clearly be seen. Shown in FIGS. 7A-E are a histogram of the correlation between the amount of carbohydrate in the meal and the glycemic response across the study participants (FIG. 7A), examples of two participants with a low correlation between the amount of carbohydrates and the glycemic response (FIGS. 7B and 7C) and two participants with a high such correlation (FIGS. 7D and 7E).

The models were learned using a linear model with an L1 (sum of absolute values) regularization using the LASSO algorithm. Across all meals predicted (recall that each meal was predicted using a model learned on meals excluding it), model 1, 2, and 3 achieved a correlation of predictions of 0.35, 0.36, and 0.44, respectively. The positive predictive values of all models demonstrate the power of using the group database of the present embodiments to predict the glycemic response to unseen meals. The increased accuracy of the predictions using model 3 demonstrates that a personally tailored predictor that utilizes personal parameters of the individual can lead to greatly enhanced performance. On the two clusters of individuals that exhibited the highest correlation between the carbohydrate content and the glucose response, the model predicted held out unseen meals with a correlation of 0.50 and 0.51 for cluster 1 and 2, respectively. These clusters together account for nearly 50% of all individuals, demonstrating that for nearly half of the study participants, who are identified in advance, the predictor achieves very good predictions.

Figure 8A:
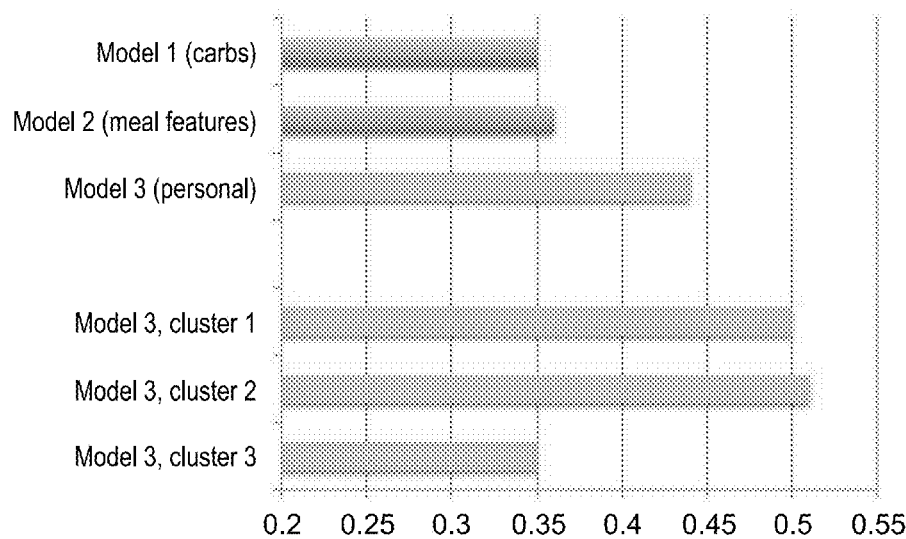
Figure 8B:
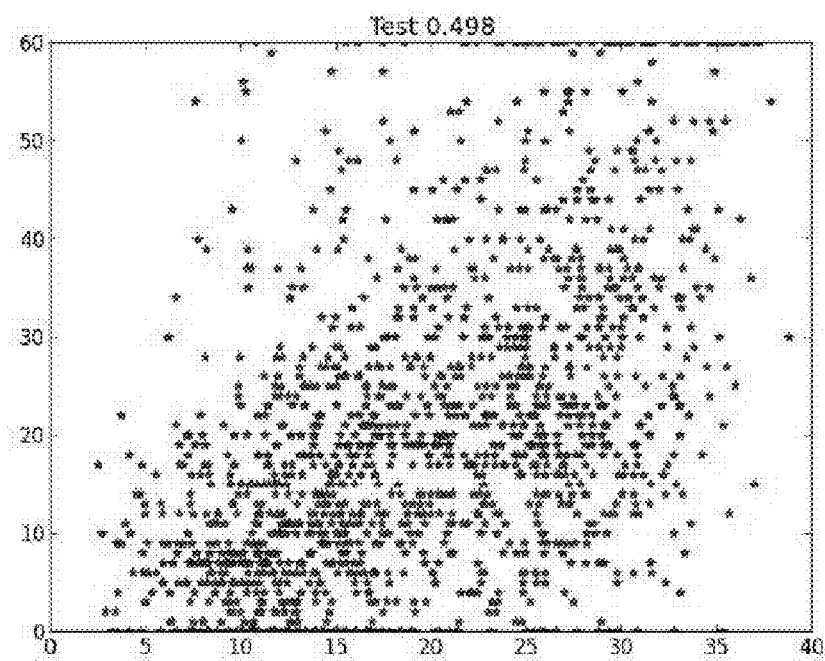
Figure 8C:
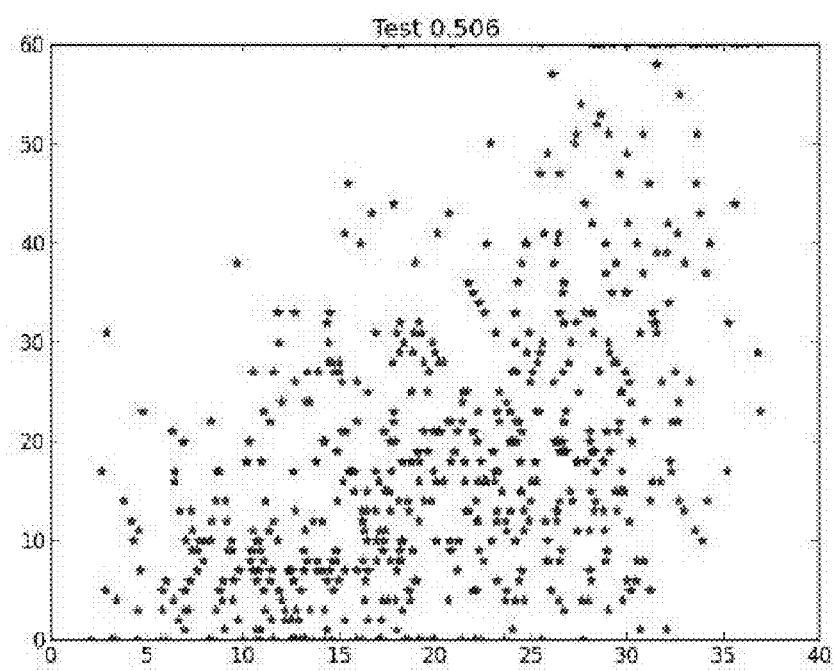
Figure 8D:
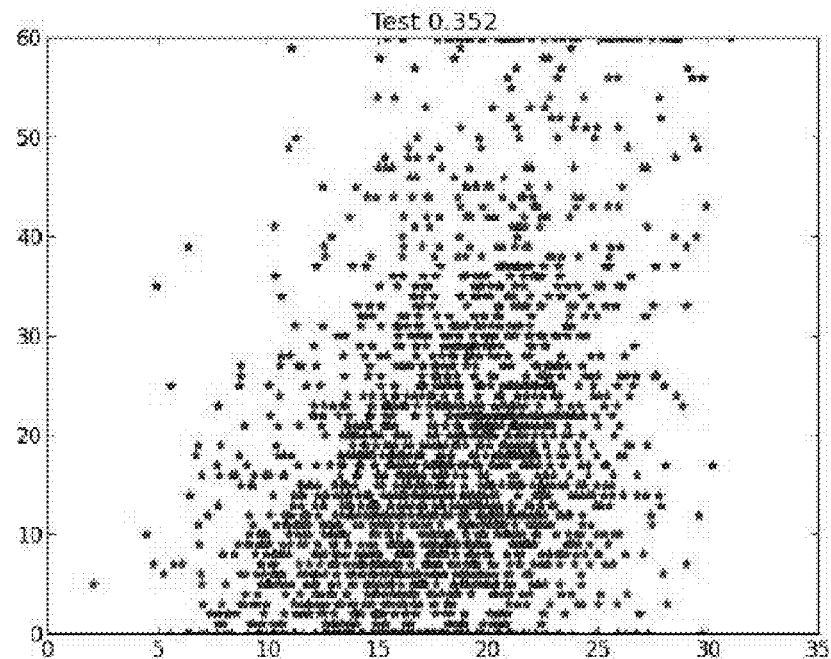

These results are summarized in FIGS. 8A-D, which show a personally tailored predictor of individual glycemic responses. FIG. 8A shows a comparison of the correlation of predicting held out unseen meals between three models that either use general parameters of the meal (models 1 and 2) or also personal parameters of individuals (model 3). Also shown are the predictions for each of the clusters of individuals that are utilized in model 3. FIGS. 8B-D show the predictions obtained from the personally tailored model (model 3) on the three clusters of individuals defined based on the relationship that the individuals in each cluster exhibit between the amount of carbohydrates in their meal and their glucose response. Note the high correlations of 0.5 and 0.51 in clusters 1 and 2 of individuals that exhibit a high correlation between the carbohydrate content of the meal and the glucose response.

Conclusions

The present example demonstrates the utility of the method of the present embodiments to predict the glycemic response of individuals to food intake. The present example shows that a predictor that is personally tailored to parameters of the individual can achieve improved performance. The present example shows that for a subset of individuals consisting roughly of half the population and whose identity can be determined ahead of time, the predictions are more accurate. These individuals have the property of exhibiting a high degree of correlation (compared to others in the population) between the amount of carbohydrates in the meal and the glucose response.

Example 2

The data collected in Example 1 above were re-analyzed by stochastic boosting using decision trees. The results are presented in FIGS. 9A-G.

Figure 9A:
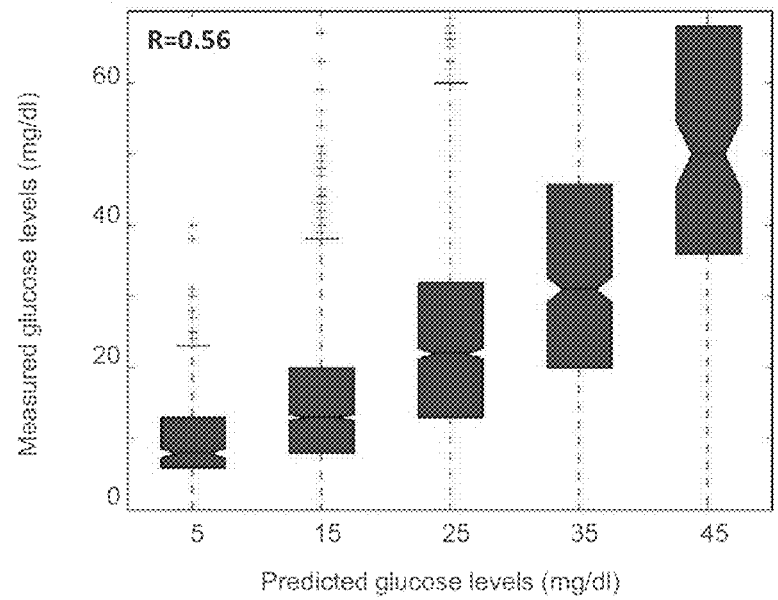

FIG. 9A shows boxplot of actual measured glucose responses for each of 5 different glucose level predictions. The center line is the median, and top and bottom bars signify the 75 and 25 percentiles, respectively. The overall correlation across all meals (R=0.56) is also indicated.

Figure 9B:
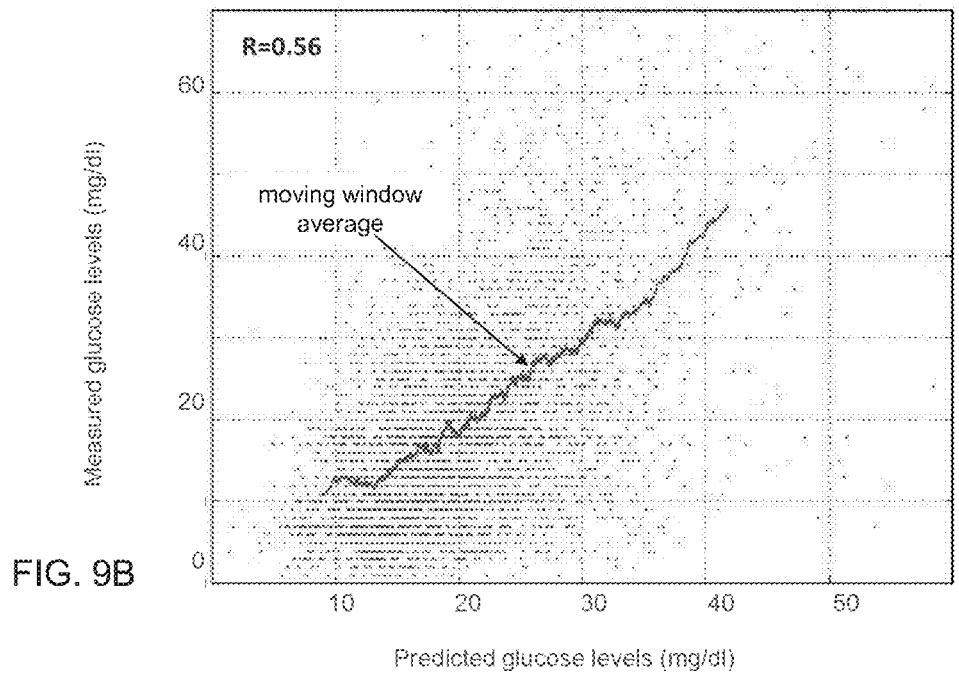

FIG. 9B shows all 7072 meals as predicted according to some embodiments of the present invention. Shown is a comparison between the predicted glucose response (abscissa) and the measured response (ordinate). Also shown is the overall correlation (R=0.56) and a line indicating a moving window average (100 consecutive predictions).

Figure 9C:
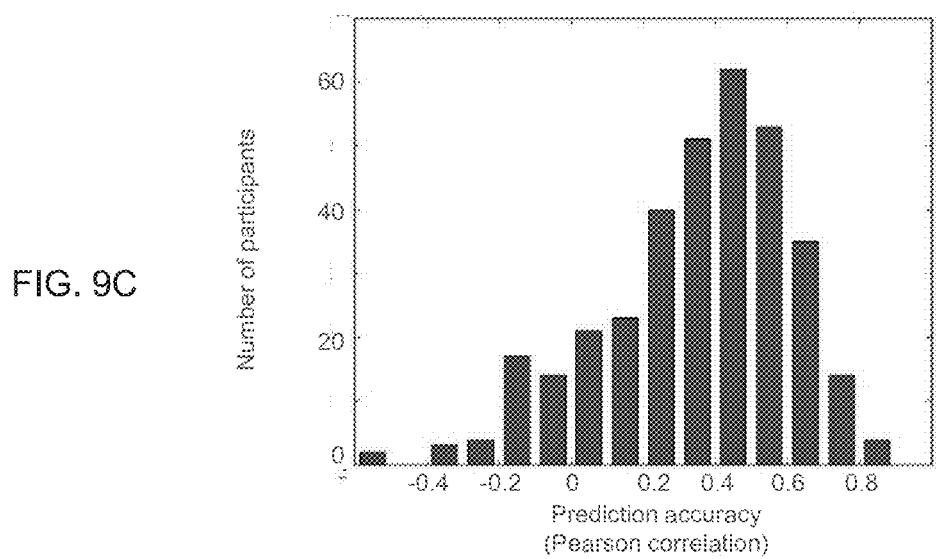
Figures 9D, 9E:
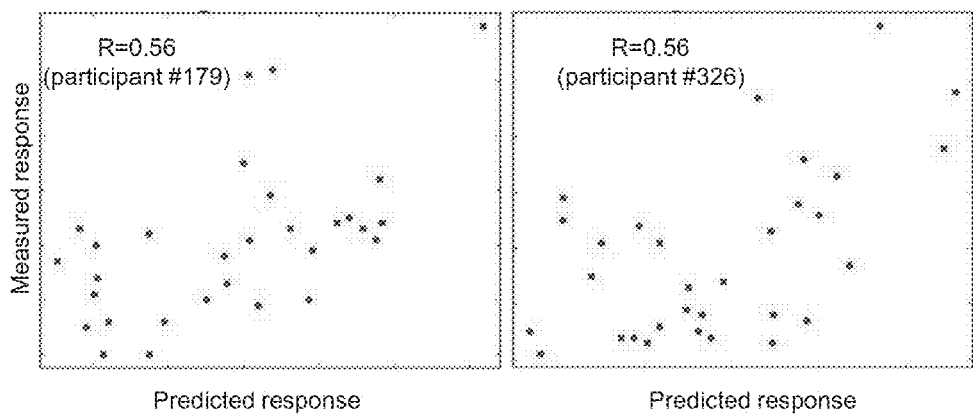

FIG. 9C shows a histogram of the number of participants at different levels of correlation predictions.

Figures 9F, 9G:
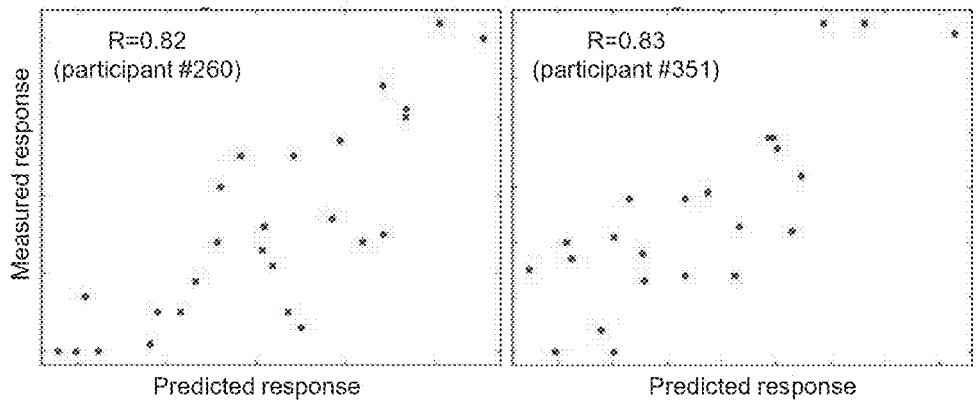

FIGS. 9D-G shows comparisons of the predicted and measured response of two participants from typical predictions (FIGS. 9D and 9E), and two best predicted participants (FIGS. 9F and 9G).

Example 3

This example demonstrates the ability of the database according to embodiments described herein to predict a response of a subject to food using a group database that includes responses of other subjects to foods, and a subject-specific database which includes data that describes the subject but does not include any response to any food. The data and the analysis of the collected data at the learning phase were the same as in Example 2. In the prediction phase, the glucose level data of the subject under analysis were removed from the database. The subject-specific database included data describing general lifestyle, health, blood chemistry, and food intake habits including a list of foods which are regularly consumed by the individual together with corresponding intake frequencies. The lifestyle, health and food intake habits were collected by questionnaires.

FIG. 10A shows boxplot of the measured glucose responses for each of 5 different glucose level predictions. The notations and markings are the same as in FIG. 9A. As shown, the overall correlation across all meals was R=0.46.

FIG. 10B shows all 7072 meals as predicted according to some embodiments of the present invention. The notations and markings are the same as in FIG. 9B.

Example 4

This example illustrates how the database can be used to predict a subject's glycemic response to food.

Material and Methods 16 impaired glycemic response and healthy participants engaged in a three week experiment of diet intervention. The first week was a profiling week, from which two personalized test diets were computed: (1) one full week of a personalized diet predicted to have "good" (low) postprandial blood glucose responses; and (2) one full week of a personalized diet predicted to have "bad" (high) postprandial blood glucose responses. The present inventors evaluated whether indeed the personalized diet of the "good" week elicited lower blood glucose responses as compared to the personalized diet given on the "bad" week.

Before the experiment, a dietitian planned a personal tailored diet for 6 days as follows: each participant decided how many meals and calories he or she eats in a day. All meals in the 6 days were different and in every day the same number of meals and calories were consumed with a gap of at least 3 hours between meals. The content of the meals was decided by the participant to match their taste and regular diet. For example, a participant may choose to eat 5 meal categories a day as following: a 300 calorie breakfast, 200 calorie brunch, 500 calorie launch, 200 calorie snack and 800 calorie dinner. The participant decides on 6 different options for each meal category (5 meal categories in the example: breakfasts, brunch, launch, snack and dinner) with the help of the dietitian to ensure that all breakfasts are isocaloric with a maximum deviation of 10%.

The experiment began with taking a blood sample and anthropometric measurements from the participant, connecting the participant to a continuous glucose monitor and starting the 6 day diet, while logging all eaten meals during the time of the study. On the $7^{th}$ day of the experiment, the participant performed a standard (50 g) oral glucose tolerance test after which he ate normally throughout that day. The first week which is referred to as the "mix week" exposed the participant to a variety of foods which afterwards determined which meals were relatively "good" and "bad" i.e. which meals resulted in low and high glucose response respectively. The glucose blood levels were monitored using a continuous glucose monitor (Medtronic iPro2) with a high 5 minute temporal resolution. The glucose rise and glucose incremental area under the curve (AUC) was measured for each meal. The meals from low to high response were selected where the best and worst two meals of every meal category were selected and marked as good meals and bad meals.

After the good and bad meals were selected, the participants continued with the additional two weeks of the experiment, which were the test weeks. The "good week" comprised only of good meals and "bad week" comprised only of meals predicted to elicit "bad" (high) blood glucose responses. A week comprised 6 days of diet and one day of 50 grams glucose tolerance test as described above. The order of the weeks was randomly chosen and neither participant nor dietitian were exposed to the order of the weeks. After three weeks, the glucose level between weeks was compared.

To date, 16 individuals completed the experiment out of which 10 had an impaired glycemic response and 6 were healthy.

Results

"Good" and "bad" meals were correctly categorized: It was found that the vast majority of the meals tested in the two test weeks showed a glucose response in accord with the predictions (low/high).

A significant improvement in the average AUC following a meal in the "good" week compared to the "bad" week was observed. This result holds for both healthy and impaired glucose tolerance individuals where in the latter group the differences between the "good" and "bad" week were greater (FIG. 11).

The results also showed that blood glucose responses following meals show a diurnal pattern (FIG. 12). When fitting a line though average AUC responses of all meals in a category it can be seen that breakfast AUC trend is relatively low followed by lunch and dinner with the highest trend of AUC. This trend remains after normalizing either by carbohydrates or calories in a meal (FIGS. 13A-B).

REFERENCES

1. Danaei, G. et al. National, regional, and global trends in fasting plasma glucose and diabetes prevalence since 1980: systematic analysis of health examination surveys and epidemiological studies with 370 country-years and 2.7 million participants. Lancet 378, 31-40, doi:10.1016/50140-6736(11)60679-X (2011).
2. Li, G. et al. The long-term effect of lifestyle interventions to prevent diabetes in the China Da Qing Diabetes Prevention Study: a 20-year follow-up study. Lancet 371, 1783-1789, doi:10.1016/S0140-6736(08)60766-7 (2008).
3. Gerstein, H. C. et al. Annual incidence and relative risk of diabetes in people with various categories of dysglycemia: a systematic overview and meta-analysis of prospective studies. Diabetes research and clinical practice 78, 305-312, doi: 10.1016/j.diabres.2007.05.004 (2007).
4. Tabak, A. G. et al. Trajectories of glycaemia, insulin sensitivity, and insulin secretion before diagnosis of type 2 diabetes: an analysis from the Whitehall II study. Lancet 373, 2215-2221, doi:10.1016/50140-6736(09)60619-X (2009).
5. Is fasting glucose sufficient to define diabetes? Epidemiological data from 20 European studies. The DECODE-study group. European Diabetes Epidemiology Group. Diabetes Epidemiology: Collaborative analysis of Diagnostic Criteria in Europe. Diabetologia 42, 647-654 (1999).
6. Gong, Q. et al. Long-term effects of a randomised trial of a 6-year lifestyle intervention in impaired glucose tolerance on diabetes-related microvascular complications: the China Da Qing Diabetes Prevention Outcome Study. Diabetologia 54, 300-307, doi:10.1007/s00125-010-1948-9 (2011).
7. Meyer, K. A. et al. Carbohydrates, dietary fiber, and incident type 2 diabetes in older women. The American journal of clinical nutrition 71, 921-930 (2000).
8. Lau, C. et al. Dietary glycemic index, glycemic load, fiber, simple sugars, and insulin resistance: the Inter99 study. Diabetes care 28, 1397-1403 (2005).
9. Vega-Lopez, S., Ausman, L. M., Griffith, J. L. & Lichtenstein, A. H. Interindividual variability and intra-individual reproducibility of glycemic index values for commercial white bread. Diabetes care 30, 1412-1417, doi: 10.2337/dc06-1598 (2007).
10. Wolever, T. M. et al. Determination of the glycaemic index of foods: interlaboratory study. European journal of clinical nutrition 57, 475-482, doi:10.1038/sj.ejcn.1601551 (2003).
11. Williams, S. M. et al. Another approach to estimating the reliability of glycaemic index. The British journal of nutrition 100, 364-372, doi:10.1017/S0007114507894311 (2008).
12. Shulzhenko, N. et al. Crosstalk between B lymphocytes, microbiota and the intestinal epithelium governs immunity versus metabolism in the gut. Nature medicine 17, 1585-1593, doi:10.1038/nm 2505 (2011).
13. Everard, A. et al. Responses of gut microbiota and glucose and lipid metabolism to prebiotics in genetic obese and diet-induced leptin-resistant mice. Diabetes 60, 2775-2786, doi:10.2337/db11-0227 (2011).
14. Musso, G., Gambino, R. & Cassader, M. Interactions between gut microbiota and host metabolism predisposing to obesity and diabetes. Annual review of medicine 62, 361-380, doi:10.1146/annurev-med-012510-175505 (2011).
15. Turnbaugh, P. J. et al. A core gut microbiome in obese and lean twins. Nature 457, 480-484, doi:10.1038/nature07540 (2009).
16. Turnbaugh, P. J. et al. An obesity-associated gut microbiome with increased capacity for energy harvest. Nature 444, 1027-1031, doi:10.1038/nature05414 (2006).
17. Claesson, M. J. et al. Gut microbiota composition correlates with diet and health in the elderly. Nature 488, 178-184, 10.1038/nature11319 (2012).

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting.

What is claimed is:

1. A method of predicting a response of a subject to food for providing the subject with a personalized diet, the method comprising:
   presenting the subject with a list of foods on a user interface device, and receiving from the user interface device a selected food to which a response of the subject is unknown;
   accessing a computer readable medium storing a first database having data describing the subject but not a response of the subject to said selected food;
   accessing a computer readable medium storing a second database having data pertaining to responses of other subjects to foods, said responses of said other subjects including responses of at least one other subject to said selected food or a food similar to said selected food;
   analyzing said databases based on said selected food to estimate the response of the subject to said selected food; and
   providing the subject with a personalized diet, based on said estimate.

2. The method of claim 1, wherein said first database comprises data pertaining to responses of said subject to foods, each food being other than said selected food.

3. A method of predicting a response of a subject to food for providing the subject with a personalized diet, the method comprising:
   presenting the subject with a list of foods on a user interface device, and receiving from the user interface device a selected food and a context of food intake for which a response of the subject is unknown;
   accessing a computer readable medium storing a first database having data describing the subject but not a response of the subject to said selected food within said selected context of food intake;
   accessing a computer readable medium storing a second database having data pertaining to responses of other subjects to foods, said responses of said other subjects including responses of at least one other subject to said selected food or a food similar to said selected food;
   analyzing said databases based on said selected food to estimate the response of the subject to said selected food within said selected context of food intake; and
   providing the subject with a personalized diet, based on said estimate.

4. The method of claim 3, wherein said first database comprises data pertaining to responses of said subject to foods within respective contexts of food intake, each food being other than said selected food within said selected context of food intake.

5. The method according to claim 3, wherein said context of food intake is selected from the group consisting of an amount of said food, a time of day, a time before or after sleep, a time before or after exercise, a mental or physiological condition, and an environmental condition.

6. The method according to claim 1, wherein said analyzing comprises executing a machine learning procedure.

7. The method of claim 6, wherein said machine learning procedure comprises a supervised learning procedure.

8. The method according to claim 6, wherein said machine learning procedure comprises at least one procedure selected from the group consisting of clustering, support vector machine, linear modeling, k-nearest neighbors analysis, decision tree learning, ensemble learning procedure, neural networks, probabilistic model, graphical model, Bayesian network, and association rule learning.

9. The method according to claim 1, wherein said second database comprises data classified according to a predetermined set of classification groups, wherein said analysis comprises classifying the subject according to said set of classification groups, to provide a classification group being specific to the subject, and wherein said response of the subject to said selected food is estimated based on responses in said second database that correspond to said classification group.

10. The method according to claim 1, wherein at least one of said first and said second databases comprises one or more multidimensional entries, each entry having at least three dimensions.

11. The method according to claim 1, wherein at least one of said first and said second databases comprises one or more multidimensional entries, each entry having at least four dimensions.

12. The method according to claim 1, wherein at least one of said first and said second databases comprises one or more multidimensional entries, each entry having at least five dimensions.

13. The method according to claim 1, wherein at least one of said first and said second databases comprises one or more multidimensional entries, each entry corresponding to an individual and comprises a food consumed by said individual and at least a glycemic response of said individual to said food.

14. The method according to claim 1, wherein at least one of said first and said second databases comprises one or more multidimensional entries, each entry corresponding to an individual being characterized in the respective database by at least a partial microbiome profile of said individual.

15. The method according to claim 1, wherein at least one of said first and said second databases comprises one or more multidimensional entries, each entry corresponding to an individual and comprises a food consumed by said individual and at least a characteristic intake frequency associated with said food.

16. The method according to claim 1, wherein at least one of said first and said second databases comprises one or more multidimensional entries, each entry corresponding to an individual and comprises a food consumed by said individual and at least a partial chemical composition of said food.

17. The method according to claim 1, wherein at least one of said first and said second databases comprises one or more multidimensional entries, each entry corresponding to an individual being characterized in the respective database by at least a partial blood chemistry of said individual.

18. The method according to claim 1, wherein at least one of said first and said second databases comprises one or more multidimensional entries, each entry corresponding to an individual being characterized in the respective database by at least a genetic profile of said individual.

19. The method according to claim 1, wherein at least one of said first and said second databases comprises one or more multidimensional entries, each entry corresponding to an individual being characterized in the respective database by at least metabolomic data associated with said individual.

20. The method according to claim 1, wherein at least one of said first and said second databases comprises one or more multidimensional entries, each entry corresponding to an individual being characterized in the respective database by at least a medical condition of said individual.

21. The method according to claim 1, wherein at least one of said first and said second databases comprises one or more multidimensional entries, each entry corresponding to an individual being characterized in the respective database by at least food intake habits of said individual.

22. The method according to claim 1, wherein at least one of said first and said second databases comprises one or more multidimensional entries, each entry corresponding to an individual, and comprises a listing of activities performed by said individual over a time period.

23. A computer software product, comprising a computer-readable medium in which program instructions are stored, which instructions, when read by a data processor, cause the data processor to receive a food to which a response of a subject is unknown, and to execute the method according to claim 1.

24. Apparatus for predicting a response of a subject to food, the apparatus comprising:
a user interface configured to receive a food to which a response of the subject is unknown; and
a data processor having a computer-readable medium storing the computer software product of claim 23.

25. A method of constructing a database for providing at least one subject with a personalized diet, the method comprising, for each subject of a group of subjects:
by a measuring device communicating with the vasculature of the subject, monitoring glucose levels of said subject over a time period of at least a few days;
by a user interface device, monitoring foods consumed by said subject over said time period;
via a communication network, transmitting said monitored glucose levels and said monitored foods to a data processor for analyzing said monitored glucose levels and said monitored foods to associate a glycemic response to each food of at least a portion of said consumed foods;
making a database record pertaining to said association in at least one database; and
storing said database record in a computer readable medium for use in providing at least one subject with a personalized diet.

26. The method of claim 25, wherein said at least one database comprises a group database corresponding to all subjects in said group of subject.

27. The method of claim 26, wherein for at least one subject, said at least one database also comprises a subject-specific database corresponding to said subject.

28. The method according to claim 25, further comprising obtaining additional data pertaining to said subject and/or said food and making a record of said additional data in said at least one database.

29. The method according to claim 28, further comprising processing said at least one database using a multidimensional analysis procedure, and updating said at least one database responsively to said analysis.

30. The method according to claim 29, wherein said multidimensional analysis procedure comprises executing a machine learning procedure.

31. The method according to claim 30, wherein said machine learning procedure comprises a supervised learning procedure.

32. The method according to claim 30, wherein said machine learning procedure comprises at least one procedure selected from the group consisting of classification, regression, clustering, support vector machine, linear modeling, k-nearest neighbors analysis, decision tree learning, ensemble learning procedure, neural networks, probabilistic model, graphical model, Bayesian network, and association rule learning.

33. The method according to claim 28, wherein said additional data comprises an at least partial microbiome profile of said individual.

34. The method according to claim 28, wherein said additional data comprises a characteristic intake frequency associated with said food.

35. The method according to claim 28, wherein said additional data comprises an at least partial chemical composition of said food.

36. The method according to claim 28, wherein said additional data comprises an at least a partial blood chemistry of said individual.

37. The method according to claim 28, wherein said additional data comprises an at least a genetic profile of said individual.

38. The method according to claim 28, wherein said additional data comprises a metabolomic data associated with said individual.

39. The method according to claim 28, wherein said additional data comprises a medical condition of said individual.

40. The method according to claim 28, wherein said additional data comprises food intake habits of said individual.

41. The method according to claim 28, wherein said additional data comprises a listing of activities performed by said individual over said time period.

42. The method according to claim 1, wherein said food is a food product.

43. The method according to claim 1, wherein said food is a food type.

44. The method according to claim 1, wherein said food is a family of food types.

45. The method according to claim 1, wherein said food is a combination of a plurality of foods, each food of said plurality of foods being selected from the group consisting of a food product, a food type, and a family of food types.

46. The method according to claim 1, being executed so as to prevent, control and/or treat at least one medical condition selected from the group consisting of a condition that is directly associated with obesity, metabolic syndrome, diabetes, and a liver disease or disorder.

* * * * *